United States Patent [19]

Feldmann et al.

[11] Patent Number: 5,863,786
[45] Date of Patent: Jan. 26, 1999

[54] NUCLEIC ACID ENCODING MODIFIED HUMAN TNFα (TUMOR NECROSIS FACTOR ALPHA) RECEPTOR

[75] Inventors: Marc Feldmann, Hammersmith, United Kingdom; Patrick William Gray, Bothell, Wash.; Martin John Charles Turner, Ann Arbor, Mich.; Fionula Mary Brennan, Hammersmith, United Kingdom

[73] Assignee: The Mathilda and Terence Kennedy Institute of Rheumatology, London, United Kingdom

[21] Appl. No.: 465,982

[22] Filed: Jun. 6, 1995

Related U.S. Application Data

[62] Division of Ser. No. 50,319, filed as PCT/GB91/01826 Oct. 18, 1991, Pat. No. 5,633,145.

[30] Foreign Application Priority Data

Oct. 18, 1990 [GB] United Kingdom ............... 9022648

[51] Int. Cl.$^6$ .................. C12N 5/10; C12N 15/12; C12N 15/62
[52] U.S. Cl. .................. 435/252.3; 435/69.1; 435/69.3; 435/320.1; 536/23.4; 536/23.5
[58] Field of Search ................... 435/69.1, 69.7, 435/252.3, 320.1; 536/23.7, 23.4, 23.5

[56] References Cited

FOREIGN PATENT DOCUMENTS 308378  3/1989  European Pat. Off. .
393438  10/1990  European Pat. Off. .

OTHER PUBLICATIONS

Schall et al., *Cell* (1990) 61:361–370.
Loetscher et al., *Cell* (1990) 61:351–359.
Gray et al., *Proc. Natl. Acad. Sci. USA* (1990) 87:7380–7384.
Yan et al., *J. Biol. Chem.* (1991) 266(18):12098–12104.

*Primary Examiner*—John Ulm
*Attorney, Agent, or Firm*—Robins & Associates

[57] ABSTRACT

A DNA molecule is provided which encodes a polypeptide which is capable of binding human TNFα and which has the first three cysteine-rich subdomains, but not the fourth cysteine-rich subdomain, of the extracellular binding domain of a receptor selected from the 55 kD and 75 kD receptors for human TNFα. The ability of the polypeptide to bind to TNFα means that it can be used for treating diseases mediated by TNFα activity, such as rheumatoid arthritis.

8 Claims, 14 Drawing Sheets

```
225  Lys Pro Leu Ala Pro Asn Pro Ser Phe Ser Pro Thr Leu Gly Phe Ser Pro Val
948  AAG CCC CTG GCC CCA AAC CCA AGC TTC AGT CCC ACT CTG GGC TTC AGT CCC GTG

249  Pro Ser Thr Phe Pro Ser Ser Thr Phe Pro Thr Pro Thr Leu Gly Ala Pro Arg
1020 CCC AGT TCC ACC TTC CCA TCC AGC TCC ACC TTC CCC ACC CCC ACC CTG GCT CCC AGA

273  Glu Val Ala Pro Pro Tyr Gln Gly Val Ala Thr Ala Asp Cys Pro Asp Pro Ile Asn
1092 GAG GTG GCA CCA CCC TAT CAG GGG GTA GCC ACA GCT GAC TGT CCC GAC ATC AAC

297  Pro Leu Gln Lys Trp Glu Gln Gly Ser Ala His Leu Arg Arg Thr Ala Thr Leu Tyr
1164 CCC CTT CAG AAG TGG GAG CAG GGG AGT GCC CAC CTC CGC CGC ACG GCG ACC CTG TAC

321  Ala Val Val Asn Val Leu Pro Ser Leu Ala Leu Arg Val Arg Phe Val Glu Ala Asp His Glu
1236 GCC GTG GTG AAC GTG CTT CCC AGC CTG GCC CTC CTA GTG CGG TTC GAG GCG CAC GAG

345  Ile Asp Arg Pro Gln Asn Gly Gly Leu Leu Gly Arg Cys Tyr Ser Met Leu Ala Thr Arg
1308 ATC GAT CCG CCC CAG AAC GGG CTG CTA GGG TGC TAC AGC ATG CTG GCG ACC AGG

369  Arg Arg Thr Pro Arg Arg Glu Glu Leu Leu Gly Arg Val Leu Arg Asn Met Asp Leu Gly
1380 CGG CGC ACG CCG CGC CGC GAG GAG CTG CTG GGA CGC GTG CTC CGC AAT ATG GAC CTG GGC

393  Cys Leu Glu Asp Ile Glu Glu Ala Ala Pro Pro Ala Leu Pro Ser Leu Leu Arg
1452 TGC CTG GAG GAC ATC GAG GAG GCG GCC CCG CCC GCT CTC CTC AGT CTT CTC
1521 GGCTGCAGGGCC TGCAGGGGCAGC TCTAAGCAGC AACCCCACTT TTTTCTGGAA AGGAGGGGTC
1601 CTGCAGGGGC AAGCAGGAGC AGTCAGCGCT GTGCGCGCGG ATCGATGCGCA GCTTTTCTCA GCTGCCTGCG
1681 CGCGCGGGAC ATGCCTCATG GCCGAGGTGC CCCGTTTTGG GCCAAAGGCT AGTGGGTGGT TTGCGAGGAT
1761 GAGGGGACGCT TGCATAAGCA GTTTTTTTTG GTGTCCTCAC CAGCAGGGGC CCCTGGTTCG TCCCTGAGCC
1841 TTTTCACAG TGCATAAGCA GTTTTTTTTG GACAAGCAC GTTTTGTTT TCAATCATGT TACACTAATA
1921 GAAACTTGGC CCTCTGTGC CCTCTGCTG ATAGCAAGCT GAACTGTCCT AAGGCAGGGG CGAGCACGGA
2001 ACAATGGGGC CTTCAGCTGG AGCTGTGGAC AGCTGTGGAC TCTGAAGTTA AG
```

```
DNA sequence    608 b.p.    TGTCTGGCATGG ... CCCCAGATTAG    linear

9 /       1                                   39 /      11
      ATG GGC CTC TCC ACC GTG CCT GAC CTG CTG CCG CTG GTG CTC CTG GAG CTG TTG GTG
      met gly leu ser thr val pro asp leu leu pro leu val leu leu glu leu leu val
     69 /      21                                   99 /      31
      GGA ATA TAC CCC TCA GGG GTT ATT GGA CTG GTC CCT CAC CTA GGG GAC AGG GAG AAG AGA
      gly ile tyr pro ser gly val ile gly leu val pro his leu gly asp arg glu lys arg
    129 /      41                                  159 /      51
      GAT AGT GTG TGT CCC CAA GGA AAA TAT ATC CAC CCT CAA AAT AAT TCG ATT TGC TGT ACC
      asp ser val cys pro gln gly lys tyr ile his pro gln asn asn ser ile cys cys thr
    189 /      61                                  219 /      71
      AAG TGC CAC AAA GGA ACC TAC TTG TAC AAT GAC TGT CCA GGC CCG GGG CAG GAT ACG GAC
      lys cys his lys gly thr tyr leu tyr asn asp cys pro gly pro gly gln asp thr asp
    249 /      81                                  279 /      91
      TGC AGG GAG TGT GAG AGC GGC TCC TTC ACC GCT TCA GAA AAC CAC CTC AGA CAC TGC CTC
      cys arg glu cys glu ser gly ser phe thr ala ser glu asn his leu arg his cys leu
    309 /     101                                  339 /     111
      AGC TGC TCC AAA TGC CGA AAG GAA ATG GGT GTG CAG ATC TCT TCT TGC ACA GTG GAC
      ser cys ser lys cys arg lys glu met gly val gln ile ser ser cys thr val asp
    369 /     121                                  399 /     131
      CGG GAC ACC GTG TGT GGC TGT AGG AAG AAC CAG TAC CGG CAT TAT TGG AGT GAA AAC CTT
      arg asp thr val cys gly cys arg lys asn gln tyr arg his tyr trp ser glu asn leu
    429 /     141                                  459 /     151
      TTC CAG TGC TTC AAT TGC AGC CTC TGC CTC AAT GGG ACC CTC CAC CTC TCC TGC CAG GAG
      phe gln cys phe asn cys ser leu cys leu asn gly thr leu his leu ser cys gln glu
    489 /     161                                  519 /     171
      AAA CAG AAC ACC GTG TGC ACC TGC CAT GCA GGT TTC TTT CTA AGA GAA AAC GAG TGT GTC
      lys gln asn thr val cys thr cys his ala gly phe phe leu arg glu asn glu cys val
    549 /     181                                  579 /     191
      TCC TGT AGT AAC TGT AAA AGC CTG TGC ACG AAG TTG TGC CTA CCC CAG ATT TAG
      ser cys ser asn cys lys ser leu cys thr lys leu cys leu pro gln ile AMB
```

FIG. 7

DNA sequence 482 b.p.     TGTCTGGCATGG ... CCCCAGATTTAG  linear

```
     9 /  1                                                        39 /  11
ATG GGC CTC TCC ACC GTG CCT GAC CTG CTG CCG CTG GTG CTC CTG GAG CTG TTG GTG
met gly leu ser thr val pro asp leu leu pro leu val leu leu glu leu leu val
    69 /  21                                                       99 /  31
GGA ATA TAC CCC TCA GGG GTT ATT GGA CTG GTC CCT CAC CTA GGG GAC AGG GAG AAG AGA
gly ile tyr pro ser gly val ile gly leu val pro his leu gly asp arg glu lys arg
   129 /  41                                                      159 /  51
GAG TGT GAG AGC GGC TCC TTC ACC GCT TCA GAA AAC CAC CTC AGA CAC TGC CTC AGC TGC
glu cys glu ser gly ser phe thr ala ser glu asn his leu arg his cys leu ser cys
   189 /  61                                                      219 /  71
TCC AAA TGC CGA AAG GAA ATG GGT CAG GTG GAG ATC TCT TGC ACA GTG GAC CGG GAC
ser lys cys arg lys glu met gly gln val glu ile ser cys thr val asp arg asp
   249 /  81                                                      279 /  91
ACC GTG TGT GGC TGC AGG AAG AAC CAG TAC CGG CAT TAT TGG AGT GAA AAC CTT TTC CAG
thr val cys gly cys arg lys asn gln tyr arg his tyr trp ser glu asn leu phe gln
   309 / 101                                                      339 / 111
TGC TTC AAT TGC AGC CTC TGC CTC AAT GGG ACC GTG CAC CTC TCC TGC CAG GAG AAA CAG
cys phe asn cys ser leu cys leu asn gly thr val his leu ser cys gln glu lys gln
   369 / 121                                                      399 / 131
AAC ACC GTG TGC ACC TGC CAT GCA GGT TTC TTT CTA AGA GAA AAC GAG TGT GTC TCC TGT
asn thr val cys thr cys his ala gly phe phe leu arg glu asn glu cys val ser cys
   429 / 141                                                      459 / 151
AGT AAC TGT AAG AAA AGC CTG GAG TGC ACG AAG TTG TGC CTA CCC CAG ATT TAG
ser asn cys lys lys ser leu glu cys thr lys leu cys leu pro gln ile AMB
```

FIG. 8

```
DNA sequence    470 b.p.    TGTCTGGCATGG ... CCCCAGATTTAG    linear

9 /   1                                  39 /  11
ATG GGC CTC TCC ACC GTG CCT GAC CTG CTG CCG CTG GTG CTC CTG GAG CTG TTG GTG
met gly leu ser thr val pro asp leu leu pro leu val leu leu glu leu leu val
 69 /  21                                  99 /  31
GGA ATA TAC CCC TCA GGG GTT ATT GGA CTG GTC CCT CAC CTA GGG GAC AGG GAG AAG AGA
gly ile tyr pro ser gly val ile gly leu val pro his leu gly asp arg glu lys arg
129 /  41                                 159 /  51
GAT AGT GTG TGT CCC CAA GGA AAA TAT ATC CAC CCT CAA AAT TCG ATT TGC TGT ACC
asp ser val cys pro gln gly lys tyr ile his pro gln asn ser ile cys cys thr
189 /  61                                 219 /  71
AAG TGC CAC AAA GGA ACC TAC TTG TAC AAT GAC TGT CCA GGC CCG GGG CAG GAT ACG GAC
lys cys his lys gly thr tyr leu tyr asn asp cys pro gly pro gly gln asp thr asp
249 /  81                                 279 /  91
TGC AGG AAG AAC CAG TAC CGG CAT TAT TGG AGT GAA AAC CTT TTC CAG TGC TTC AAT TGC
cys arg lys asn gln tyr arg his tyr trp ser glu asn leu phe gln cys phe asn cys
309 / 101                                 339 / 111
AGC CTC TGC CTC AAT GGG ACC GTG CAC CTC TGC CAG AAA CAG AAC ACC GTG TGC
ser leu cys leu asn gly thr val his leu cys gln lys gln asn thr val cys
369 / 121                                 399 / 131
ACC TGC CAT GCA GGT TTC TTT CTA AGA GAA AAC GAG TGT GTC TCC TGT AGT AAC TGT AAG
thr cys his ala gly phe phe leu arg glu asn glu cys val ser cys ser asn cys lys
429 / 141                                 459 / 151
AAA AGC CTG GAG TGC ACG AAG TTG TGC CTA CCC CAG ATT TAG
lys ser leu glu cys thr lys leu cys leu pro gln ile AMB
```

FIG. 9

```
DNA sequence   485 b.p.        TGTCTGGCATGG ... CCCCAGATTTAG  linear

9  /   1                                          39 /  11
         ATG GGC CTC TCC ACC GTG CCT GAC CTG CTG CCG CTG CTC GTG CTG TTG GTG
         met gly leu ser thr val pro asp leu leu pro leu leu val leu leu val
     69 /  21                                          99 /  31
         GGA ATA TAC CCC TCA GGG GTT ATT GGA CTG GTC CCT CAC CTA GGG GAC AGG GAG AAG AGA
         gly ile tyr pro ser gly val ile gly leu val pro his leu gly asp arg glu lys arg
    129 /  41                                         159 /  51
         GAT AGT GTG TGT CCC CAA GGA AAA TAT ATC CAC CCT CAA AAT AAT TCG ATT TGC TGT ACC
         asp ser val cys pro gln gly lys tyr ile his pro gln asn asn ser ile cys cys thr
    189 /  61                                         219 /  71
         AAG TGC CAC AAA GGA ACC TAC TTG TAC AAT GAC TGT CCA GGC CAG GAT ACG GAC
         lys cys his lys gly thr tyr leu tyr asn asp cys pro gly gln asp thr asp
    249 /  81                                         279 /  91
         TGC AGG GAG TGT GAG AGC GGC TCC TTC ACC GCT TCA GAA AAC CAC CTC AGA CAC TGC CTC
         cys arg glu cys glu ser gly ser phe thr ala ser glu asn his leu arg his cys leu
    309 / 101                                         339 / 111
         AGC TGC TCC AAA TGC CGA AAG GAA ATG GGT CAG GTG GAG ATC TCT TCT TGC ACA GTG GAC
         ser cys ser lys cys arg lys glu met gly gln val glu ile ser ser cys thr val asp
    369 / 121                                         399 / 131
         CGG GAC ACC GTG TGT ACC TGC CAT GCA GGT TTC CTA AGA GAA AAC GAG TGT GTC TCC
         arg asp thr val cys thr cys his ala gly phe leu arg glu asn glu cys val ser
    429 / 141                                         459 / 151
         TGT AGT AAC TGT AAG AAA AGC CTG GAG TGC ACG AAG TTG TGC CTA CCC CAG ATT TAG
         cys ser asn cys lys lys ser leu glu cys thr lys leu cys leu pro gln ile AMB
```

FIG. 10

DNA sequence    512 b.p.    TGTCTGGCATGG ... GTGTGCACCTGA    linear

```
         1                      11                      21                      31
 9 /                    39 /                    69 /                    99 /
ATG GGC CTC TCC ACC GTG CCT GAC CTG CTG CCG CTG GTG CTC CTG GAG CTG TTG GTG
met gly leu ser thr val pro asp leu leu pro leu val leu leu glu leu leu val
         41                     51                     61                     71
129 /                   159 /                  189 /                  219 /
GGA ATA TAC CCC TCA GGG GTT ATT GGA CTG GTC CCT CAC CTA GGG GAC AGG GAG AAG AGA
gly ile tyr pro ser gly val ile gly leu val pro his leu gly asp arg glu lys arg
         81                     91                    101                    111
249 /                  279 /                  309 /                  339 /
GAT AGT GTG TGT CCC CAA GGA AAA TAT ATC AAG GGA ACC TAC TTG TAC AAT GAC TGT CCA GGC CCG CAG GAT ACG GAC
asp ser val cys pro gln gly lys tyr ile lys gly thr tyr leu tyr asn asp cys pro gly gln asp thr asp
        121                    131                    141                    151
369 /                  399 /                  429 /                  459 /
AAG TGC CAC AAA GGA ACC TGT GAG AGC TGT GAG AGC GGC TCC TTC ACC GCT TCA GAA AAC CAC CTC AGA CAC TGC CTC
lys cys his lys gly thr cys glu ser gly cys ser phe thr ala ser glu asn his leu arg his cys leu
        161
489 /
TGC AGG GAG TGT CGA AAG GAA ATG GGT GGT GAG GTG CAG GTG GAG ATC TCT TCT TGC ACA GTG GAC
cys arg glu cys arg lys glu met gly val glu ile ser ser cys thr val asp
AGC TGC TCC AAA TGC CGA AAG GAA AAC CAG CAG TAC CGG CAT TAT TGG AGT GAA AAC CTT
ser cys ser lys cys arg lys glu asn gln tyr arg his tyr trp ser glu asn leu
CGG GAC ACC GTG TGT GGC TGC AGG AAG AAC CAG TAC CGG AAG AAC CAG TAC AAC CTT CGG ACC AAT GGG ACC GTG CAC CTC TCC TGC CAG GAG
arg asp thr val cys gly cys arg lys asn gln tyr arg lys asn gln tyr asn gly thr val his leu ser cys gln glu
TTC CAG TGC TTC AAT TGC AGC CTC TGC CTC AAT GGG ACC GTG CAC CTC TCC TGC CAG GAG
phe gln cys phe asn cys ser leu cys leu asn gly thr val his leu ser cys gln glu
AAA CAG AAC ACC GTG TGC ACC TGA
lys gln asn thr val cys thr OPA
```

FIG. 11

NUCLEIC ACID ENCODING MODIFIED HUMAN TNFα (TUMOR NECROSIS FACTOR ALPHA) RECEPTOR

This application is a divisional of U.S. patent application Ser. No. 08/050,319, filed a PCT/GB91/01826 Oct. 18, 1991, now U.S. Pat. No. 5,633,145.

The present invention relates to recombinant proteins and their use.

Tumour necrosis factor-α (TNFα) is a potent cytokine which elicits a broad spectrum of biological responses. TNFα causes the cytolysis or cytostasis of many tumour cell lines in vitro, induces the haemorrhagic necrosis of transplanted tumours in mice, enhances the phagocytosis and cytotoxicity of polymorphonuclear neutrophils, and modulates the expression of many proteins, including lipoprotein lipase, class I antigens of the major histo-compatibility complex, and cytokines such as interleukin 1 and interleukin 6. TNFα appears to be necessary for a normal immune response, but large quantities produce dramatic pathogenic effects. TNFα has been termed "cachectin" since it is the predominant factor responsible for the wasting syndrome (cachexia) associated with neoplastic disease and parasitemia. TNF is also a major contributor to toxicity in gram-negative sepsis, since antibodies against TNF can protect infected animals.

The many activities of TNFα are mediated by binding to a cell surface receptor. Radioligand binding studies have confirmed the presence of TNF receptors on a wide variety of cell types. Although these receptors are expressed in limited numbers (1,000–10,000 receptors/cell), they bind TNFα with high affinity ($Ka=10^9 M^{-1}$ at 4° C.). Lymphotoxin (LT, also termed TNFβ) has similar, if not identical, biological activities to TNFα, presumably because both are recognized by the same receptor.

Recently, several laboratories have detected heterogeneity in TNF receptor preparations. Two distinct cell surface receptors which bind TNFα and TNFβ have recently been characterised at the molecular level. cDNA for one form of the receptor with a Mr of 55 kD was isolated utilising probes designed from the peptide sequence of a soluble form of the receptor (1,2). A second receptor of Mr 75 kD was cloned by a COS cell expression approach (3). Both receptors are members of a larger family of cytokine receptors which include the nerve growth factor receptor, the B cell antigen CD40, the rat T cell antigen MRC OX40. In addition these receptors are homologous to the predicted product of a transcriptionally active open reading frame from shope fibroma virus which appears to give rise to a secreted protein.

The most conserved feature amongst this group of cell surface receptors is the cysteine rich extracellular ligand binding domain, which can be divided into four repeating motifs of about forty amino acids. We have now generated four soluble receptor derivatives of the 55 kD TNFα receptor (TNFR). Each derivative is composed of the extracellular binding domain but without one of the cysteine rich subdomains. We have found that the derivative which lacks the membrane-proximal fourth subdomain retains the ability to bind TNFα with high affinity. This finding has general applicability.

Accordingly, the present invention provides a polypeptide which is capable of binding human TNFα and which consists essentially of:

(a) the first three cysteine-rich subdomains, but not the fourth cysteine-rich subdomain, of the extracellular binding domain of the 55 kD or 75 kD receptor for human TNFα; or (b) an amino acid sequence having a homology of 90% or more with the said sequence (a).

The invention also provides:
- a DNA sequence which encodes such a polypeptide;
- a vector which incorporates a DNA sequence of the invention and which is capable, when provided in a transformed host, of expressing the polypeptide of the invention encoded by the DNA sequence; and
- a host transformed with such a vector.

In the accompanying drawings:

FIGS. 1A and 1B show the nucleotide sequence of the human TNFα CDNA (SEQ ID NO:24) and encoded amino acid sequence (SEQ ID NO:25). The predicted signal sequence residues are numbered −40 to −1. The transmembrane domain is boxed and potential N-linked glycosylation sites are overlined. The sequence homologous with the designed oligonucleotide probe is found at nucleotide positions 477–533.

FIG. 2 is a Northern blot (lanes 1–3) of 10 μg of oligo-dT selected RNA from human 293 cells (fibroblast cell line) (lane 1), placenta (lane 2) and spleen (lane 3) hybridised with the TNF receptor cDNA (SmaI-EcoRI fragment). The Southern blot (lanes 4–6) was hybridized with the same probe. Human genomic DNA (5 μg per lane) was digested with PstI (lane 4), Hind III (lane 5) and EcoRI (lane 6).

FIGS. 3A-1, 3A-2 and 3B show the binding characteristics of recombinant human TNF receptor expressed in COS-7 cells. The direct binding of recombinant $^{125}$I-TNFα to COS-7 cells transfected with prTNFR is presented in FIG. 3A-1. FIG. 3A-2 contains Scatchard analysis derived from this data. As shown in FIG. 3B, monolayers of Cos-7 cells transfected with TNFR cDNA were incubated with 1 nM $^{125}$I-TNF in the presence of various concentrations of unlabelled TNFα or TNFβ.

FIGS. 4A and 4B show the effects of soluble TNFR on TNFα binding and biological activity. FIG. 4A shows the effects of supernatants from Cos-7 cells transfected with a cDNA encoding a soluble form of the TNF receptor (pTNFRecd, closed circles) or mock transfected (open circles) on $^{125}$I-TNF binding to U937 cells. FIG. 4B shows the effects of these supernatants on TNF mediated killing of WEHI 164 (clone 13) line. Assays were performed as described in Materials and Methods.

FIGS. 7 to 11 show the nucleotide sequence and the predicted amino acid sequence of the encoded polypeptide of pTNFRecd, pΔI, pΔII, pΔIII and pΔIV.

Figure 2:
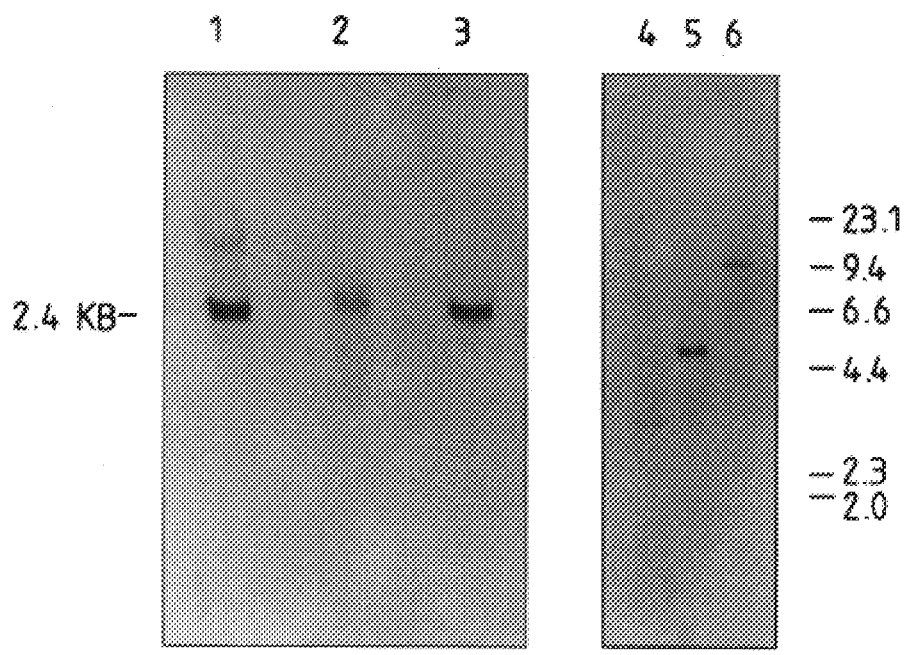

A polypeptide according to the invention is capable of binding human TNFα. Typically the polypeptide has a binding affinity for human TNFα of $10^7 M^{-1}$ or greater, for example $10^8 M^{-1}$ or greater. The affinity may be from $10^7$ to $10^{10}$ $M^{-1}$, for example from $10^8$ to $10^9 M^{-1}$.

A preferred polypeptide consists essentially of the first three cysteine-rich subdomains of the extracellular binding domain of the 55 kD receptor for human TNFα. The sequence (a₁) of these three subdomains is shown in SEQ ID NO:4.

A useful polypeptide has the amino acid sequence (c) shown in SEQ ID NO:2.

In an alternative embodiment, the polypeptide may consist essentially of the first three cysteine-rich subdomains of the extracellular binding domain of the 75 kD receptor.

Apart from the amino acid sequence (a), the polypeptides may alternatively consist essentially of an amino acid sequence (b) having a homology of 90% or more with sequence (a). The degree of homology may be 95% or more or 98% or more. Amino acid sequence (a) may therefore be modified by one or more amino acid substitutions, insertions and/or deletions and/or by an extension at either or each end. There should be no modification of the cysteine-residues, however. A polypeptide comprising sequence (b) must of course still be capable of binding human TNFα.

For example, one or more amino acid residues of the sequence (a), other than a cysteine residue, may be substituted or deleted or one or more additional amino acid residues may be inserted; provided the physicochemical character of the original sequence is preserved, i.e. in terms of charge density, hydrophobicity/hydrophilicity, size and configuration. Conservative substitutions may be made. Candidate substitutions are, based on the one-letter code (Eur. J. Biochem. 138, 9–37, 1984):

A for G and vice versa,
V by A, L or G;
K by R;
S by T and vice versa;
E for D and vice versa; and
Q by N and vice versa.

Up to 15 residues may be deleted from the N-terminal and/or C-terminal of the polypeptide, for example up to 11 residues or up to 5 residues.

The polypeptides of the invention consist essentially of sequence (a) or (b). They do not contain a fourth cysteine-rich subdomain. However, the polypeptides may be longer polypeptides of which sequence (a) or (b) is a part. A short sequence of up to 50 amino acid residues may be provided at either or each terminal of sequence (a) or (b). The sequence may have up to 30, for example up to 20 or up to 10, amino acid residues.

Alternatively, a much longer extension may be present at either or each terminal of sequence (a) or (b) of up to, for example, 100 or 200 amino acid residues. Longer amino acid sequences may be fused to either or each end. A chimaeric protein may be provided in which the or each extension is a heterologous amino acid sequence, i.e. a sequence not naturally linked to the amino acid sequence above. Such a chimaeric protein may therefore combine the ability to bind specifically to human TNFα with another functionality.

The polypeptides of the invention lack the fourth cysteine-rich subdomain of the 55 kD or 75 kD receptor as the case may be. In particular, they lack the cysteine residues of the fourth subdomain. They therefore do not comprise, immediately after the third cysteine-rich subdomain, any of the amino acid sequence up to the last cysteine residue of the fourth cysteine-rich subdomain of the relevant receptor except possibly the first amino acid residue of that sequence. The polypeptides may extend beyond that first amino acid residue as indicated above, though, by way of other amino acid sequences.

The polypeptides are typically recombinant polypeptides, although they may be made by synthetic methods such as solid-phase or solution-phase polypeptide synthesis in which case an automated peptide synthesiser may be employed. They may therefore commence with a N-terminal residue M. They are prepared by recombinant DNA technology. The preparation of the polypeptides therefore depends upon the provision of a DNA sequence encoding the polypeptide. A suitable sequence encoding the first three cysteine-rich subdomains of the extracellular binding domain of the 55 kD receptor comprises: GTG TGT CCC CAA GGA AAA TAT ATC CAC CCT CAA AAT AAT TCG ATT TGC TGT ACC AAG TGC CAC AAA GGA ACC TAC TTG TAC AAT GAC TGT CCA GGC CCG GGG CAG GAT ACG GAC TGC AGG GAG TGT GAG AGC GGC TCC TTC ACC GCT TCA GAA AAC CAC CTC AGA CAC TGC CTC AGC TGC TCC AAA TGC CGA AAG GAA ATG GGT CAG GTG GAG ATC TCT TCT TGC ACA GTG GAC CGG GAC ACC GTG TGT GGC TGC AGG AAG AAC CAG TAC CGG CAT TAT TGG AGT GAA AAC CTT TTC CAG TGC TTC AAT TGC AGC CTC TGC CTC AAT GGG ACC GTG CAC CTC TCC TGC CAG GAG AAA CAG AAC ACC GTG TGC (SEQ ID NO:3).

A DNA sequence may further comprise a DNA sequence encoding a signal sequence fused to the 5' end of the coding sequence. Any signal sequence may be appropriate. The signal sequence should be capable of directing secretion of the polypeptide of the invention from the cell in which the polypeptide is expressed. The signal sequence may be the natural signal sequence for the 55 kD TNFα receptor. An appropriate DNA sequence encoding the first three cysteine-rich subdomains of the extracellular binding domain of the 55 kD receptor and such a signal sequence is therefore: ATG GGC CTC TCC ACC GTG CCT GAC CTG CTG CTG CCG CTG GTG CTC CTG GAG CTG TTG GTG GGA ATA TAC CCC TCA GGG GTT ATT GGA CTG GTC CCT CAC CTA GGG GAC AGG GAG AAG AGA GAT AGT GTG TGT CCC CAA GGA AAA TAT ATC CAC CCT CAA AAT AAT TCG ATT TGC TGT ACC AAG TGC CAC AAA GGA ACC TAC TTG TAC AAT GAC TGT CCA GGC CCG GGG CAG GAT ACG GAC TGC AGG GAG TGT GAG AGC GGC TCC TTC ACC GCT TCA GAA AAC CAC CTC AGA CAC TGC CTC AGC TGC TCC AAA TGC CGA AAG GAA ATG GGT CAG GTG GAG ATC TCT TCT TGC ACA GTG GAC CGG GAC ACC GTG TGT GGC TGC AGG AAG AAC CAG TAC CGG CAT TAT TGG AGT GAA AAC CTT TTC CAG TGC TTC AAT TGC AGC CTC TGC CTC AAT GGG ACC GTG CAC CTC TCC TGC CAG GAG AAA CAG AAC ACC GTG TGC ACC (SEQ ID NO:1).

A DNA sequence encoding a polypeptide of the invention may be synthesised. Alternatively, it may be constructed by isolating a DNA sequence encoding the 55 kD or 75 kD receptor from a gene library and deleting DNA downstream of the coding sequence for the first three cysteine-rich subdomains of the extracellular binding domain of the receptor. This gives DNA encoding the first three subdomains of either receptor. As an intermediate step, DNA encoding the entire or nearly the entire extracellular binding domain may be isolated and digested to remove DNA downstream of the coding sequence for the first three subdomains.

A modified nucleotide sequence, for example encoding an amino acid sequence (b), may be obtained by use of any appropriate technique, including restriction with an endonuclease, insertion of linkers, use of an exonuclease and/or a polymerase and site-directed mutagenesis. Whether a modified DNA sequence encodes a polypeptide of the invention can be readily ascertained. The polypeptide encoded by the sequence can be expressed in a suitable host and tested for its ability to bind specifically human TNFα.

For expression of a polypeptide of the invention, an expression vector is constructed. An expression vector is prepared which comprises a DNA sequence encoding a polypeptide of the invention and which is capable of expressing the polypeptide when provided in a suitable host. Appropriate transcriptional and translational control elements are provided, including a promoter for the DNA sequence, a transcriptional termination site, and translational start and stop codons. The DNA sequence is provided in the correct frame such as to enable expression of the polypeptide to occur in a host compatible with the vector.

The expression vector is then provided in an appropriate host. Cells harbouring the vector are grown so as to enable expression to occur. The vector may be a plasmid or a viral vector. Any appropriate host-vector system may be employed.

Figure 1A:
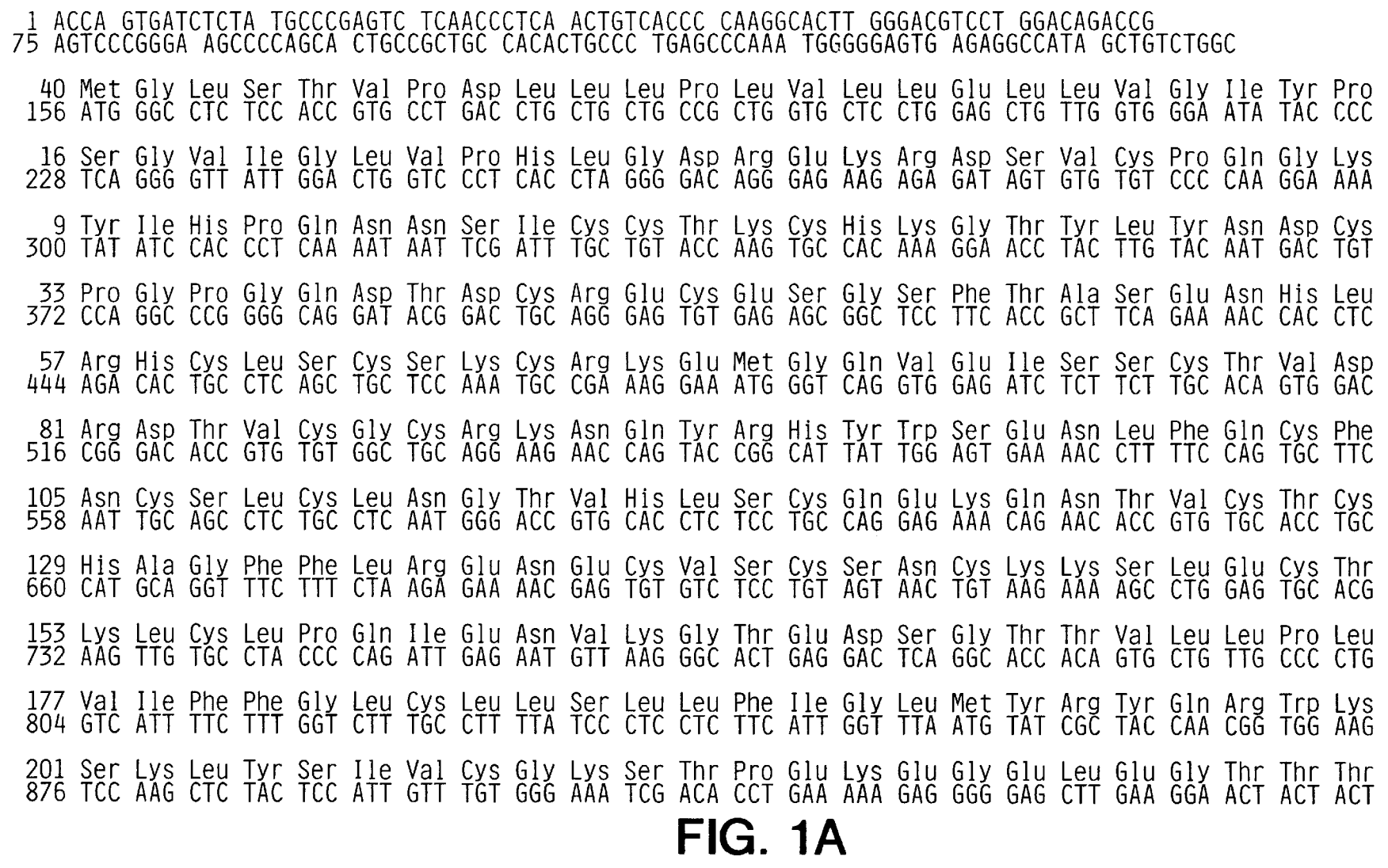

The transformed host may be a prokaryotic or eukaryotic host. A bacterial or yeast host may be employed, for example *E. coli* or *S. cerevisiae*. Insect cells can alternatively be used, in which case a baculovirus expression system may be appropriate. As a further alternative, cells of a mammalian cell line, such as Chinese Hamster Ovary (CHO) Cells may be transformed. A polypeptide glycosylated at one, two or three of the sites shown in FIGS. 1A and 1B can be obtained by suitable choice of the host cell culture.

The polypeptide of the invention can be isolated and purified. The N-terminal of the polypeptide may be heterogeneous due to processing of the translation product within a cell or as the product is being secreted from a cell. A mixture of polypeptides according to the invention, having different N-terminii, may therefore be obtained. The polypeptide is soluble.

The polypeptides of the invention have activity binding human TNFα. This activity is indictive of the possible use of the polypeptides in the regulation of TNFα-mediated responses by binding and sequestering human TNFα, for example possible use in treatment of pulmonary diseases, septic shock, HIV infection, malaria, viral meningitis, graft versus host reactions and autoimmune diseases such as rheumatoid arthritis.

For this purpose, a polypeptide of the present invention may be formulated in a pharmaceutical composition. The pharmaceutical composition also comprises a pharmaceutically acceptable carrier or diluent.

The polypeptide of the invention may be administered to a patient by any convenient route. The choice of whether an oral route or a parenteral route, such as subcutaneous, intravenous or intramuscular administration, is adopted; of the dose; and of the frequency of administration depends upon a variety of factors. These factors include the purpose of the administration, the age and weight of the patient being treated and the condition of the patient. Typically, however, the polypeptide is administered in an amount of from 1 to 1000 μg per dose, more preferably from 10 to 100 μg per dose, for each route of administration.

The following Examples illustrate the invention. A Reference Example is provided.

REFERENCE EXAMPLE
1. Materials and Methods
Reagents

Recombinant human TNFα and TNFβ were supplied as highly purified proteins derived from *E coli*. The specific activities of these preparations were approximately $10^7$ units/mg, as measured in the murine L929 cell cytotoxicity assay (4). The synthetic oligonucleotides were prepared by Oswel DNA Service (University of Edinburgh).

Isolation of TNFα 55 kD Receptor cDNA Clones

The sequence of a peptide fragment (SEQ ID NO:5) of the TNF binding protein was used to design a synthetic oligonucleotide probe (5' AAG GAG ATG GGC CAG GTT GAG ATC TCT TCT ACT GTT GAC AAT GAC ACT GTG TGT GGC-3')(SEQ ID NO:6). The 57-mer DNA probe was labelled with $^{32}$P and T4 polynucleotide kinase (New England Biolab, Beverly, Mass.) and used to screen a placenta cDNA library in gt10 (5,6). Approximately 800,000 phage were transferred to nitrocellulose filters and screened at reduced stringency (7). Filters were incubated for 2 hours at 42° C. in 0.05M sodium phosphate, pH 6.5, 20% formamide, 0.75M sodium chloride, 0.075M sodium citrate, 1% polyvinyl pyrrolidone (Sigma, St Louis, Mo.), 1% Ficoll, 1% bovine serum albumin (Sigma), and 50 ng/ml sonicated salmon sperm DNA (Sigma). The radiolabelled probe was then added to the filters ($10^8$ cpm/ml final concentration) which were hybridized for 16 hours. Filters were washed extensively in 0.06M sodium chloride, 0.006M sodium citrate, 1% SDS at 37° C. and positive clones were identified by autoradiography. Ten hybridizing clones were plaque purified (5) and cDNA insert size was determined by polyacrylamide gel electrophoresis of EcoRI digested phage DNA. The inserts of two cDNA clones were sequenced using the dideoxy chain termination technique (8).

Southern and Northern Blot Analysis

DNA was isolated from human lymphocytes by the method of Blin and Stafford (9) and used for Southern blot analysis (10). DNA was digested with restriction endonucleases (New England Biolabs), fractionated on a 1% agarose gel, and transferred to nitrocellulose. Hybridization and washing were conducted under stringent conditions (6) using a $^{32}$P-labelled preparation of a 600 bp fragment of the TNF receptor cDNA. Northern blot analysis was performed (11) on oligo-dT selected RNA isolated from human placenta, spleen (generously provided by the Cooperative Human Tissue Network, Birmingham, Ala.) and a fibroblast cell line (293 cells). Following electrophoresis on a formaldehyde 1.2% agarose gel, the RNA was transferred to nitrocellulose and hybridized with the TNFα receptor DNA probe under stringent conditions.

Mammalian Cell Expression of the Human TNFα 55 kD Receptor and Derivatives

The coding region of the majority of the human TNFα 55 kD receptor was isolated as an EcoRI fragment and cloned into a mammalian cell expression vector (12), resulting in plasmid prTNFR. The EcoRI fragment encodes 374 amino acids of the TNF receptor; the 81 carboxyl terminal residues of the cytoplasmic domain are therefore missing from this plasmid construction. A derivative of the TNFα receptor was produced by engineering a termination codon just prior to the transmembrane domain. The polymerase chain reaction (PCR) technique (13) was used to generate a 300 bp restriction fragment containing a BglII site at the 5' end and a HindIII site preceded by a TAG stop codon at the 3' end. The PCR primers were 5'GCTGCTCCAAATGCCGAAAG (SEQ ID NO:7) and 5'AGTTCAAGCTTTTACAGTGC-CCTTAACATTCTAA (SEQ ID NO:8).

The PCR product was gel purified and cloned into the TNF receptor expression plasmid (described above) digested with BglII and HindIII. DNA sequencing confirmed that the resulting plasmid (pTNFRecd) contained the designed DNA sequence. *E. coli* harbouring pTNFRecd were deposited at the National Collection of Industrial and Marine Bacteria, Aberdeen, GB on Sep. 11, 1990 under accession number NCIMB 40315.

The TNFα receptor expression plasmids were transfected into monkey COS-7 cells using Lipofectin (Gibco BRL, Bethesda, Md.) according to the manufacturer's instructions. Cells were cultured in Dulbecco's modified Eagle's medium containing 10% fetal calf serum.

Analysis of Recombinant TNFα 55 kD Receptor Derivatives

TNFα was radioiodinated with the Iodogen method (Pierce) according to the manufacturer's directions. The specific activity of the $^{125}$I-TNFα was 10–30 μCu/μg. COS cells transfected with the TNFα receptor cDNA (prTNFR, 1300 bp EcoRI fragment) were incubated for 24 hours and then seeded into six well tissue culture plates (Nunc) at $4.5 \times 10^8$ cells per well. The cells were incubated for a further 48 hours and then receptor expression was quantitated by radioligand binding for 2 hours at 4° C. Non-specific binding of $^{125}$I-TNFα was determined in the presence of a 1,000 fold molar excess of unlabelled TNFα. Binding data was analysed by the method of Scatchard (14).

The TNFα receptor derivative was analysed for inhibition of $^{125}$I-TNFα binding to the natural receptor on human U937 cells. Culture supernatant was harvested 72 hours after COS cells were transfected with pTNFRecd. U937 cells ($2 \times 10^8$ cells in 200 μl) were incubated with 1 nM $^{125}$I-TNFα and dilutions of COS cell media for 2 hours at 4° C. Cells were then centrifuged through 20% sucrose to remove unbound TNFα. Non-specific binding was determined in the presence of 1 μM unlabelled TNFα.

The TNFα receptor derivative was also analyzed for inhibition of TNFα cytotoxic effects in vitro. The cytotoxicity assay was performed as described on the TNF sensitive cell line WEHI 164 clone 13 (15). Serial dilutions of supernatants from COS cells transfected with pTNFRecd or mock transfected controls were incubated with a constant amount of TNFα (1 ng/ml) for 1 hour at 27° C. before addition to the assay.

2. RESULTS

Isolation and Characterization of the TNFα 55 kD Receptor cDNA

A partial amino acid sequence of the TNF binding protein was used to design a synthetic oligonucleotide probe. The radiolabelled probe was used to screen a human placenta cDNA library in lambdagt10 and ten hybridizing phage were isolated. The nucleotide and deduced amino acid sequences of the longest cDNA clone are depicted in FIGS. 1A and 1B. The third potential ATG initiation codon occurs at position 156 of the nucleotide sequence; the first two ATG codons are closely followed by termination codons, and the third ATG is preceded by the best translation initiation consensus nucleotides (16). The cDNA encodes an open reading frame of 1365 bases which codes for a polypeptide of 455 residues. Both of the peptide sequences determined by amino acid sequencing were identified in the encoded cDNA (17 of 19 and 18 of 19 matching residues). The amino terminal end identified for the TNF binding protein corresponds to the cDNA encoded sequence beginning at residue 41. The first 35 amino acids are generally quite hydrophobic and probably represent a signal sequence. Residues 35–40 (SEQ ID NO:7) are highly charged and such a sequence is not typically found in secretory signal sequences (17); perhaps the natural receptor is processed by proteolysis after residue 40 which contains a dibasio cleavage site (KR). Hydropathy analysis of the protein sequence predicts a single transmembrane domain of 23 amino acids. This hydrophobic sequence divides the protein into an extracellular domain of 171 residues and a cytoplasmic domain of 221 residues. The amino acid composition determined for the TNF binding protein corresponds well with the predicted composition of the extracellular domain encoded by the cDNA (results not shown). The discrepancy between the predicted receptor size (40,000 daltons) and the size determined by SDS-polyacrylamide gel electrophoresis (65,000 daltons, 18–20) is probably due to glycosylation; there are four potential N-linked glycosylation sites in the sequence, three of which are in the extracellular domain. The sequence contains a large number (17) of cysteine residues, 24 of which are in the extracellular domain. The arrangement of these cysteine residues is similar to that of several other cell surface proteins, suggesting that the TNF receptor is structurally related to a family of receptors.

A Northern blot analysis is presented in FIG. 2. The $^{32}$P-labelled cDNA hybridized to a single predominant band of oligo-dT selected RNA from human placenta or spleen. A minor larger transcript was also observed in RNA from a fibroblast cell line. The size of the hybridizing species is 2400 bases, in good agreement with the size of isolated cDNA. Also shown in FIG. 2 is a Southern blot of human genomic DNA hybridized with a 600 bp probe from the cDNA. In each of the three different restriction digests, only a single hybridized signal was observed. Thus the TNF receptor that we have isolated appears to be encoded by a single gene.

Expression of Recombinant TNF Receptor Sequences in Mammalian Cells

Figures 1, 3A:
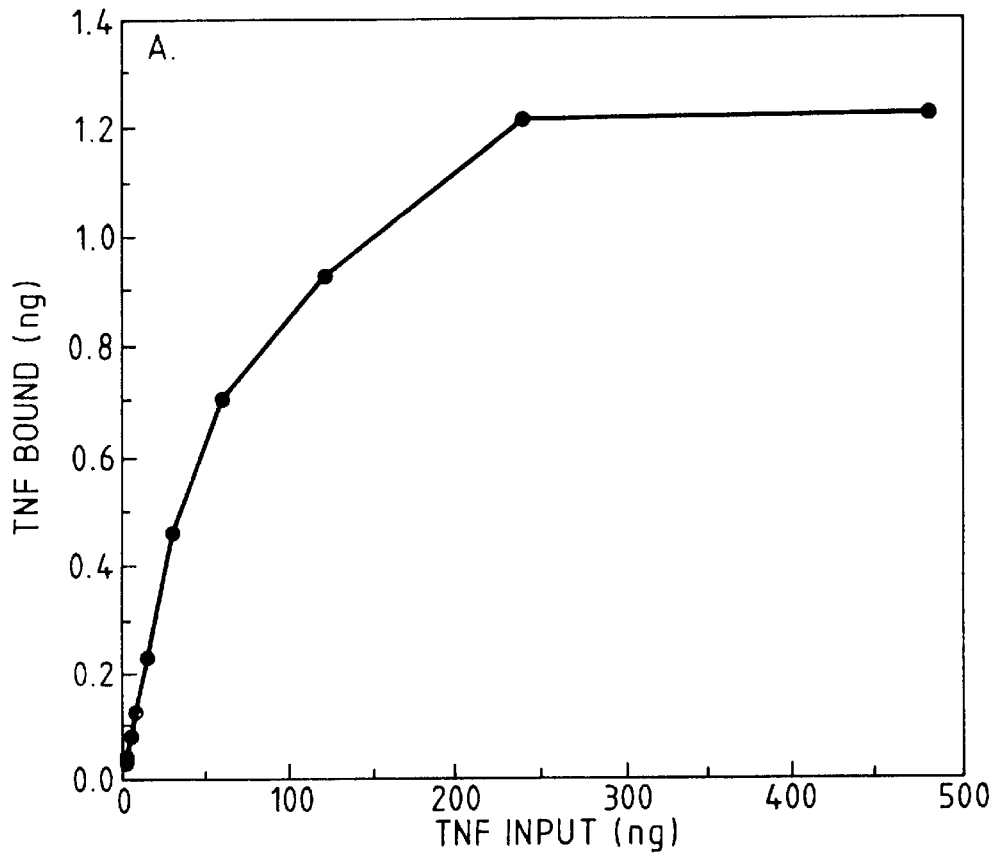
Figures 2, 3A:
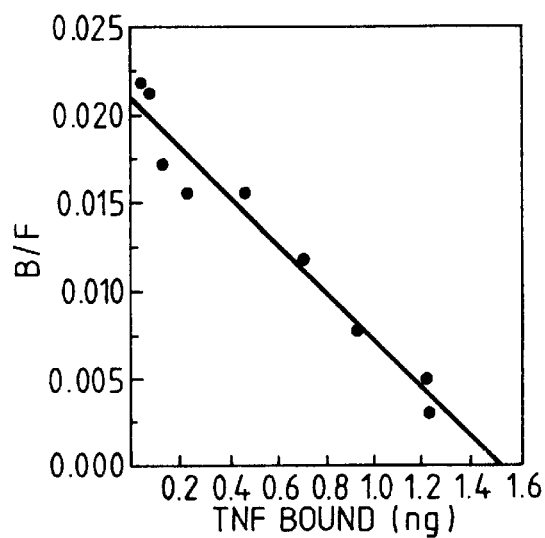
Figure 3B:
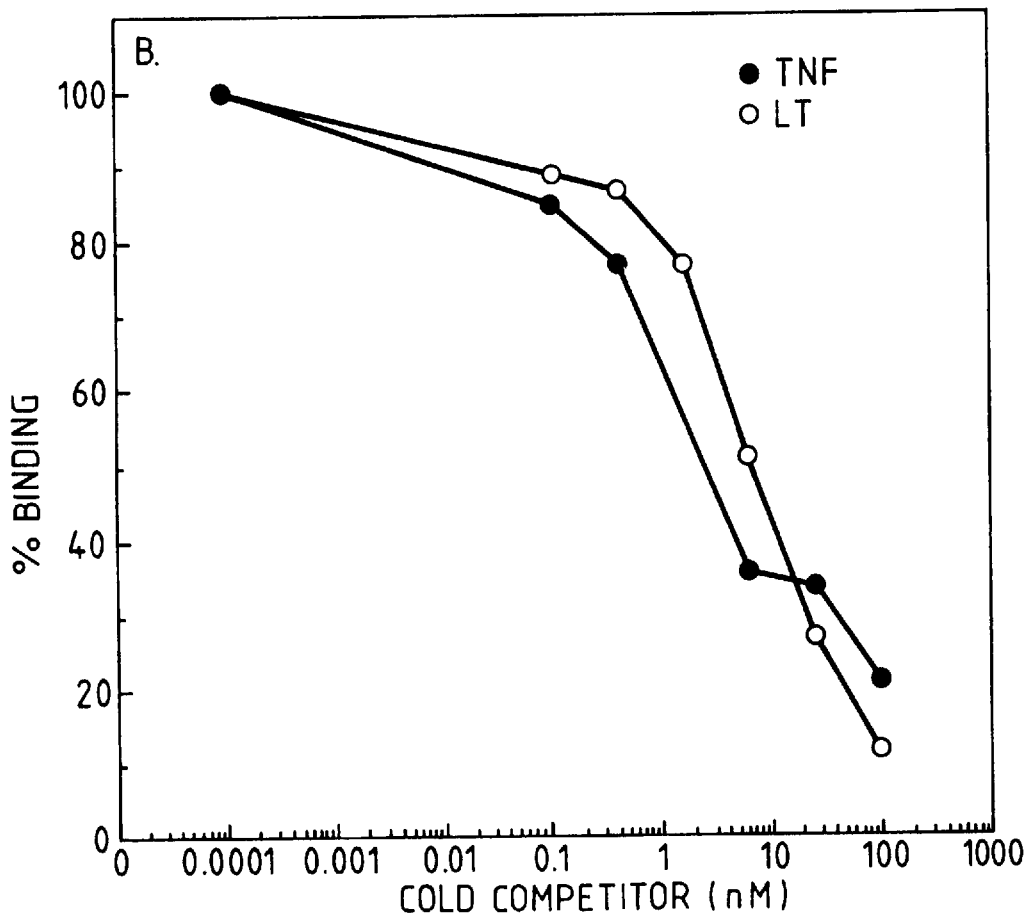

To confirm that the cDNA shown in FIGS. 1A and 1B indeed encodes the TNF receptor, the cDNA was engineered for expression in mammalian cells. The cDNA contains an EcoRI site at position 1270 of FIGS. 1A and 1B. The receptor coding sequence was isolated as a 1300 bp EcoRI-fragment (containing all but the last 81 codons of the cytoplasmic domain) and inserted into a mammalian cell expression vector containing a cytomegalovirus promoter and SV40 transcription termination sequences (12). The resulting plasmid was transfected into COS cells which were analyzed for TNF receptor expression after three days. As shown in FIGS. 3A-1, 3A-2 and 3B, the transfected cells specifically bound radioiodinated TNFα in a saturable and dose dependent fashion. The population of COS cells expressed approximately $1 \times 10^8$ receptors per cell. The measured binding affinity of recombinant receptors was $2.5 \times 10^9 M^{-1}$ at 4° C. which is in close agreement with natural receptor on human cells (19,20). The binding of $^{125}$I-TNFα (1 nM) to these cells could be inhibited by the addition of unlabelled TNFα or lymphotoxin (FIG. 3B). COS cells transfected with just the expression vector did not significantly bind $^{125}$I-TNFα (less than 2% of the binding seen with the cDNA transfection).

Figure 4A:
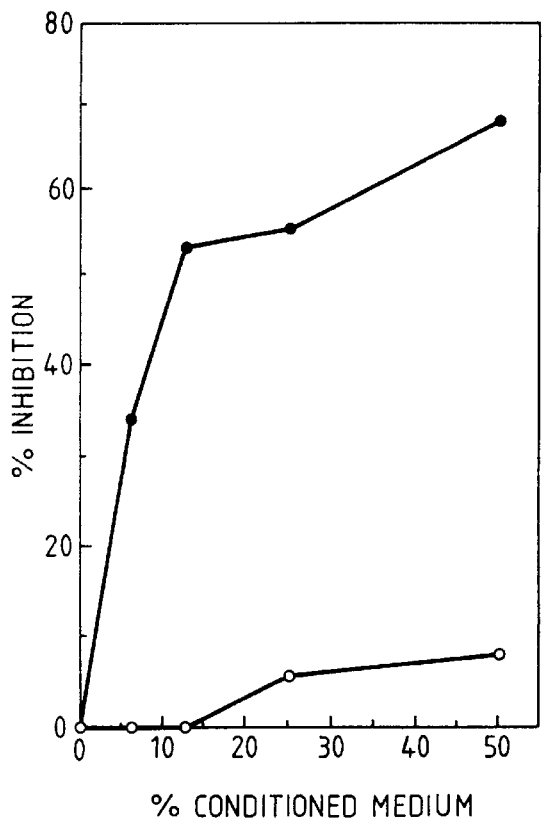
Figure 4B:
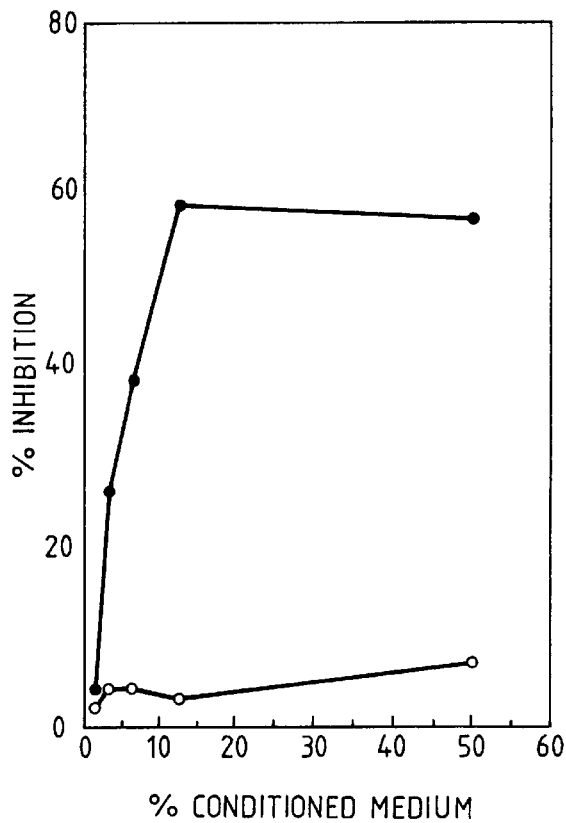

The extracellular domain of the TNF receptor is naturally shed from cells. To produce a similar recombinant derivative, a stop codon preceding the transmembrane domain was engineered into the cDNA by PCR mutagenesis. The modified DNA was inserted into the expression plasmid and subsequently transfected into COS cells. After three days, the COS cell media was tested for inhibition of TNFα binding to human U937 cells. As shown in FIG. 4A, the transfected cell media inhibited up to 70% of the binding of TNFα. The recombinant TNF receptor derivative was next tested for inhibition of TNFα biological activity. A sensitive bioassay for TNFα is a measurement of cytolysis of mouse WEHI 164 (clone 13) cells. The transfected cell media inhibited 60% of TNFα cytotoxicity on this cell line (FIG. 4B). Media from mock transfected COS cells did not inhibit TNFα induced cytotoxicity or binding. These experiments demonstrate that the recombinant extracellular domain of the TNF receptor is capable of binding TNF and inhibiting its biological activity.

TABLE 1

Structure of the mutagenic oligonucleotides

| Oligo Name | Sequence |
| --- | --- |
| 5'Cla | 5'-GTTCTATCGATAAGAGGCCATAGCTGTCTGGC-3' (SEQ ID NO: 10) |
| IA | 5'-GCTCTCACACTCTCTCTTCTCCCTGTCCCCTAG-3' (SEQ ID NO: 11) |
| IB | 5'-AGGGAGAAGAGAGAGTGTGAGAGCGGCTCCTTC-3' (SEQ ID NO: 12) |
| IIIA | 5'-TGCATGGCAGGTACACACGGTGTCCCGGTCCAC-3' (SEQ ID NO: 13) |
| IIIB | 5'-GACACCGTGTGTACCTGCCATGCAGGTTTCTTT-3' (SEQ ID NO: 14) |
| 4D | 5'-GGCCAAGCTTCAGGTGCACACGGTGTTCTG-3' (SEQ ID NO: 15) |
| 5A | 5'-GCTGCTCCAAATGCCGAAAG-3' (SEQ ID NO: 16) |
| 5D | 5'-AGTTCAAGCTTTACAGTGCCCTTAACATTCTAA-3' (SEQ ID NO: 17) |

Example 1

Expression of Polypeptide Consisting Essentially of the First Three Cysteine-rich Subdomains of the Extracellular Binding Domain of the 55 kD Receptor

1. MATERIALS AND METHODS

Reagents

*E. coli* derived recombinant human TNFα had a specific activity of $2 \times 10^7$ U/mg in an L929 cytotoxicity assay. Oligonucleotides were purchased from Oswel DNA service (University of Edinburgh).

Generation of the Recombinant Soluble TNFR Derivatives

Figure 5:
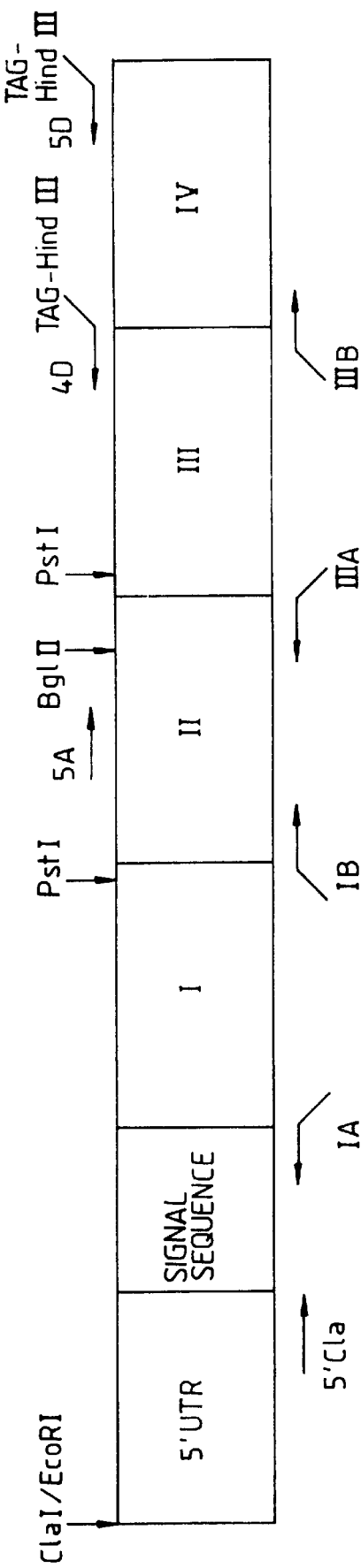
FIG. 5 is a diagram of the DNA sequence of pTNFRecd and is also a strategy map for polymerase chain reaction (PCR)-based domain deletion, in which 5'UTR is the 5'-untranslated region and I to IV are the four cysteine-rich subdomains. The oligonucleotides employed in PCR in the Example and relevant restriction sites are also shown.
Figure 6:
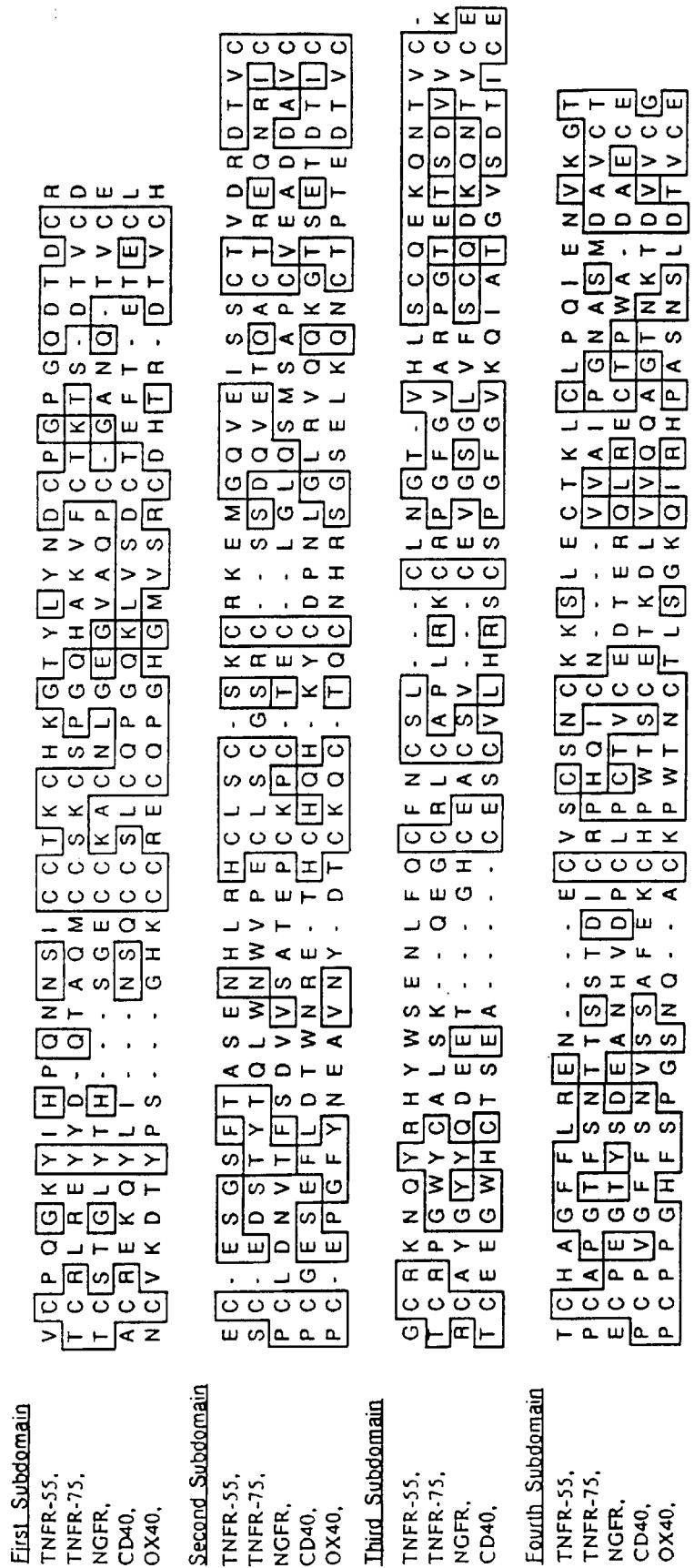
FIG. 6 shows lined up the amino acid sequences of the four cysteine-rich subdomains of the 55 kD (TNFR-55) and 75 kD (TNFR-75) receptors and of rat nerve growth factor receptor (NGFR), human CD40 and rat OX40. Homology is shown by means of boxes.

Deletion of each of the subdomains in the recombinant soluble TNFR was achieved by means of PCR fragment joining and PCR mutagenesis. The sequence of the oligonucleotides used in these experiments is given in Table 1 and their locations relative to the four cysteine rich subdomains is shown in FIG. 5. The four subdomains are lined up with respect to one another in FIG. 6.

The plasmid pTNFRecd (Reference Example) is shown in FIG. 7. pTNFRecd was further modified to remove 5'untranslated sequences by cloning of the Cla I/Bgl II digested product of a PCR using oligos 5' Cla and IIIA into ClaI/Bgl II digested pTNFRecd, to generate 5'-ΔCla. Digestion of 5'-ΔCla with Pst-1 and religation resulted in the generation of pΔII, which lacks the second cysteine rich subdomain (FIG. 9). The fourth cysteine rich subdomain was removed by cloning of the BglII/Hind III digested product of a PCR using oligonucleotides 5A and 4D into BglII/Hind III 5'-ΔCla; this introduced a termination codon after amino acid 167 (counting from the initial methionine) to yield pΔIV (FIG. 11). The constructs p I (FIG. 8) and pΔIII (FIG. 10) which lack the first and third cysteine rich subdomains respectively were generated by joining PCR fragments by means of overlaps introduced into the primers used for the PCR. The gel purified products of PCR's using 5' Cla and IA and IB and 5D were mixed and subjected to further amplification using 5'Cla and 5D as primers. The resulting fragment was digested with ClaI and BglII and cloned into ClaI/BglII digested pTNFRecd, to yield pΔI.

Similarly the gel purified products of PCR's using 5'Cla and IIIA and IIIB and 5D were mixed and subjected to further amplification using 5'Cla and 5D as primers. This product was digested with BglII and HindIII and cloned into Bgl II/Hind III cut 5'-ΔCla to yield pΔIII. In all cases the cloned derivatives were analysed by restriction enzyme analysis and DNA sequencing using sequenase (United States Biochemical Corporation).

Analysis of Recombinant Soluble TNFR Derivatives

COS cells were maintained in Dulbecco's modified Eagles medium containing 5% foetal calf serum. The soluble TNFα receptor derivatives were transfected into monkey COS cells by means of lipofectin (GIBCO-BRL, Bethesda Md.) according to the manufacturers protocol and cell free supernatants harvested 72 hours post transfection.

Inhibition of TNFα Activity

The soluble TNFα receptor derivatives were analyzed for inhibition of TNFα cytotoxic activity in vitro. The cytotoxicity assay was performed as described on the TNFα sensitive cell line WEHI 164 clone 13. Serial dilutions of supernatants from COS cells transfected with the mutant receptors or mock transfected controls were incubated with a constant amount of TNF (1 ng/ml) for 1 hour at 37° C. before addition to the assay.

2. RESULTS

Figure 12A:
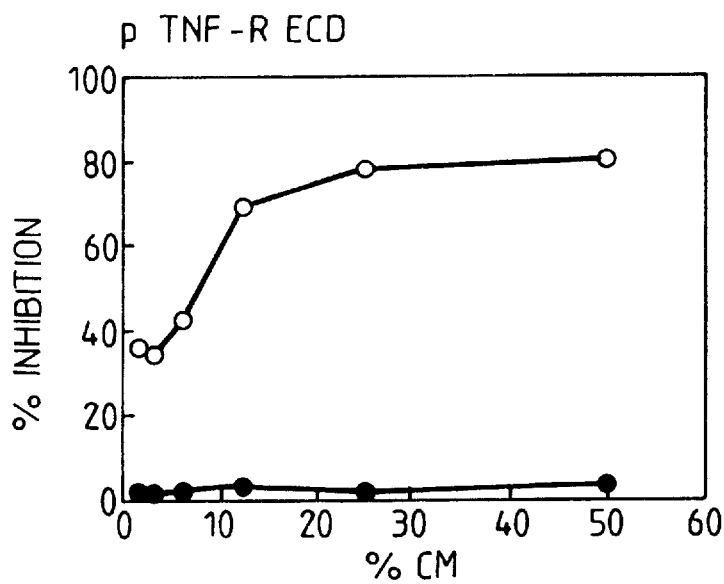
FIGS. 12A and 12B show the results of the assays described in the Example 1.
Figure 12B:
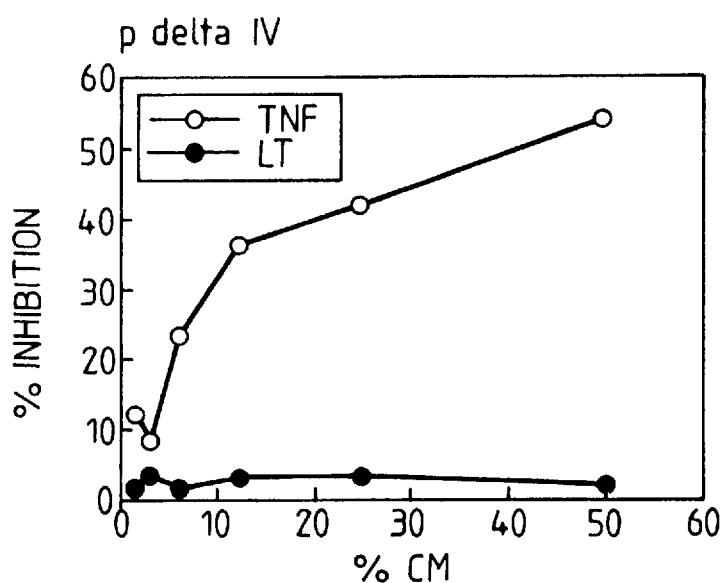

In order to understand more about the contribution of the individual cysteine rich subdomains to the binding of TNFα by the soluble form of the 55 kD TNF receptor, we removed each subdomain by PCR mutagenesis (FIG. 5). COS cells were transfected with each of these constructs and the supernatants were assayed for their ability to inhibit the cytotoxic activity of TNFα. FIG. 12A shows that conditioned medium from COS cells tranfected with pTNFRecd inhibits TNFα as previously described. Removal of the fourth cysteine rich subdomain resulted in a protein which, similar to TNFRecd, was a potent inhibitor of TNFα (FIG. 12B). The mutants lacking the first, second and third subdomains did not show any inhibitory activity in the TNFα cytotoxicity assay.

Example 2

Expression of Polypeptide Consisting Essentially of the First Three Cysteine-rich Subdomains of the Extracellular Binding Domain of the 75 kD Receptor The coding region of the human 75 kD TNFα receptor was isolated from a T cell lambda ZAP library, using a probe based on published sequences (3) and cloned into the EcoRI site of a mammalian cell expression vector (12) resulting in plasmid p75TNFR. In more detail, RNA was extracted from a cell line expressing the 75 kD receptor and reverse transcribed. Any cell line expressing this receptor could be used, such as those described by Smith et al (3). The product of the reverse transcription was subjected to 25 cycles of PCR using the following primers: 5' CGC AGA ATT CCC CGC AGC CAT GGC GCC CGT CGC C 3' (SEQ ID NO:18) and 5' GTA AGG ATC CTA TCG CCA GTG CTC CCT TCA GCT 3' (SEQ ID NO:19).

These primers are directed against the extracellular binding domain coding region of the 75 kD receptor and were taken from Smith et al (3). The amplified product was gel purified and shown to encode TNFR. This was subsequently used to screen the library. Plaque purification was performed essentially as described in the Reference Example except that the probe was labelled by random priming (21) and hybridised in 50% formamide. Filters were washed in 0.2× SSC (Standard Saline Citrate) twice at 60° C.

Figure 13:
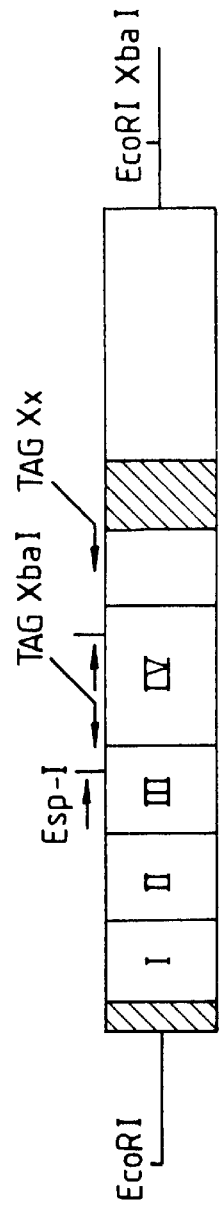
FIG. 13 shows diagrammatically the DNA encoding the 75 kD receptor in which I to IV are the four cysteine-rich subdomains. Oligonucleotides employed in PCR-domain deletion are also shown.

A derivative of the 75 kD TNFα receptor was produced by engineering a termination codon just prior to the transmembrane domain. Referring to FIG. 13, the polymerase chain reaction (PCR) technique was used to generate a 274 bp restriction fragment containing a BglII site at the 5' end and an Xba I site preceded by a TAG stop codon at the 3' end. The PCR primers were 5' ACACGACTTCATCCACG-GATA (SEQ ID NO:20) and 5' ACGTTCTAGAC-TAGTCGCCAGTGCTCCCTTCAGCTG (SEQ ID NO:21). The PCR product was digested with Bgl II and Xba I, gel purified and cloned into the TNF receptor expression plasmid (described above) digested with BglII and Xba I. DNA sequencing confirmed that the resulting plasmid contained the designed DNA sequence.

A similar approach was utilised to generate a construct which lacked the fourth cysteine-rich subdomain of the 75 kD TNFα receptor. PCR was performed using a primer upstream of the Esp I site in the 75 kD TNFR and a primer which introduced a TAG termination codon and an Xba I site. The sequences of the primers was 5' CAG AAC CGC ATC TGC ACC TGC (SEQ ID NO:22) and 5' ACGTTCTA-GACTTGCACACCACGTCTGATGTTTC (SEQ ID NO:23) respectively. The PCR product was digested with EspI and Xba I and the 110 bp DNA fragment gel purified and cloned into Esp I Xba I digested p75TNFR.

REFERENCES

1. Loetscher, H., Pan, Y. -C. E., Lahm, H. -W., Gentz, R., Brockhaus, M., Tabuchi, H. and Lesslayer, W. (1990) Cell, 61, 351–359.

2. Schall, T. J., Lewis, M., Koller, K. J., Lee, A., Rice, G. C., Wong, G. H. W., Gatanaga, T., Granger, G. A., Lentz, R., Raab, H., Kohl, W. J. and Goeddel, D. Y. (1990) Cell, 61, 361–370.

3. Smith, C. A., Davis, T., Anderson, D., Solam, L., Beckmann, M. P., Jerzy, R., Dower, S. K., Cosman, D. and Goodwin, R. G. (1990) Science 248, 1019–1023.

4. Ruff, M. R. & Gifford, G. E. (1981) Infection and Immunity, 31, 380.

5. Maniatis, T., Hardison, R. C., Lacy, E., Lauer, J., O'Connell, C., Quon, D., Sim, G. K. and Efstratiadis, A. (1978) Cell 15, 687–701.

6. Lawn, R. M., Fritsch, E. F., Parker, R. C., Blake, G & Maniatis, T. (1978) Cell 15, 1157–1174.

7. Gray, P. W., Leong, S. R., Fennie, E., Farrar, M. A., Pingel, J. T. and Schreiber, R. D. (1989) Proc. Natl. Acad. Sci USA 86, 8497–8501.

8. Smith, A. J. H., (1980) Meth. Enzym. 65 560–580.

9. Blin, N, & Stanford, D. W. (1976) Nucl. Acids Res. 3, 2303–2398.

10. Southern, E. M. (1975) J. Molec. Biol. 98, 503–517.

11. Dobner, P. R., Kawasaki, E. S., Yu, L. Y. and Bancroft, F. C. (1981) Proc. Natl. Acad. Sci. USA. 78, 2230–2234.

12. Eaton, D. L., Wood, W. I., Eaton, D., Hass, P. E., Hollinghead, P., Wion, K., Mather, J., Lawn, R. M., Vahar, G. A. and Gorman, C. (1986) Biochemistry 25: 8343–8347.

13. Scharf, S. J., Horn, G. T., Erlich, H. A. (1986) Science 233, 1076–1079.

14. Scatchard, G. (1949) Ann. New York Acad. Sci. 51, 660–672.

15. Espevik, T. & Nissen-Meyer, J. (1986) J. Immunol. Meths. 95, 99–105.

16. Kozak, M. (1989) J. Cell. Biol. 108, 229–241.

17. von Heijne, G. (1988) Nucl. Acids. Res. 14, 4683–4690.

18. Creasy, A. A., Yamamoto, R. & Vitt, C. R. (1987) Proc. Natl. Acad. Sci. USA. 84, 3293–3297.

19. Stauber, G. B., Alyer, R. A. & Aggarwal, B. B. (1988) J. Biol. Chem. 263, 19098–19104.

20. Scheurich, P., Ucer, U., Kronke, M. and Pfitzenmaier, K. (1986) Int. J. Cancer, 38, 127–133.

21. Feinburg, A. & Vogelstein, B (1984) Analytical Biochem. 137, 266–277.

SEQUENCE LISTING ( 1 ) GENERAL INFORMATION:

( i i i ) NUMBER OF SEQUENCES: 57

( 2 ) INFORMATION FOR SEQ ID NO: 1:

( i ) SEQUENCE CHARACTERISTICS:
        ( A ) LENGTH: 501 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..501

( x i ) SEQUENCE DESCRIPTION: SEQ ID NO: 1:

-continued

| | | | | | | | | | | | | | | | | |
|---|---|---|---|---|---|---|---|---|---|---|---|---|---|---|---|---|
| ATG | GGC | CTC | TCC | ACC | GTG | CCT | GAC | CTG | CTG | CTG | CCG | CTG | GTG | CTC | CTG | 48 |
| Met | Gly | Leu | Ser | Thr | Val | Pro | Asp | Leu | Leu | Leu | Pro | Leu | Val | Leu | Leu | |
| 1 | | | | 5 | | | | | 10 | | | | | 15 | | |
| GAG | CTG | TTG | GTG | GGA | ATA | TAC | CCC | TCA | GGG | GTT | ATT | GGA | CTG | GTC | CCT | 96 |
| Glu | Leu | Leu | Val | Gly | Ile | Tyr | Pro | Ser | Gly | Val | Ile | Gly | Leu | Val | Pro | |
| | | | 20 | | | | | 25 | | | | | 30 | | | |
| CAC | CTA | GGG | GAC | AGG | GAG | AAG | AGA | GAT | AGT | GTG | TGT | CCC | CAA | GGA | AAA | 144 |
| His | Leu | Gly | Asp | Arg | Glu | Lys | Arg | Asp | Ser | Val | Cys | Pro | Gln | Gly | Lys | |
| | | 35 | | | | | 40 | | | | | 45 | | | | |
| TAT | ATC | CAC | CCT | CAA | AAT | AAT | TCG | ATT | TGC | TGT | ACC | AAG | TGC | CAC | AAA | 192 |
| Tyr | Ile | His | Pro | Gln | Asn | Asn | Ser | Ile | Cys | Cys | Thr | Lys | Cys | His | Lys | |
| | 50 | | | | | 55 | | | | | 60 | | | | | |
| GGA | ACC | TAC | TTG | TAC | AAT | GAC | TGT | CCA | GGC | CCG | GGG | CAG | GAT | ACG | GAC | 240 |
| Gly | Thr | Tyr | Leu | Tyr | Asn | Asp | Cys | Pro | Gly | Pro | Gly | Gln | Asp | Thr | Asp | |
| 65 | | | | | 70 | | | | | 75 | | | | | 80 | |
| TGC | AGG | GAG | TGT | GAG | AGC | GGC | TCC | TTC | ACC | GCT | TCA | GAA | AAC | CAC | CTC | 288 |
| Cys | Arg | Glu | Cys | Glu | Ser | Gly | Ser | Phe | Thr | Ala | Ser | Glu | Asn | His | Leu | |
| | | | | 85 | | | | | 90 | | | | | 95 | | |
| AGA | CAC | TGC | CTC | AGC | TGC | TCC | AAA | TGC | CGA | AAG | GAA | ATG | GGT | CAG | GTG | 336 |
| Arg | His | Cys | Leu | Ser | Cys | Ser | Lys | Cys | Arg | Lys | Glu | Met | Gly | Gln | Val | |
| | | | 100 | | | | | 105 | | | | | 110 | | | |
| GAG | ATC | TCT | TCT | TGC | ACA | GTG | GAC | CGG | GAC | ACC | GTG | TGT | GGC | TGC | AGG | 384 |
| Glu | Ile | Ser | Ser | Cys | Thr | Val | Asp | Arg | Asp | Thr | Val | Cys | Gly | Cys | Arg | |
| | | 115 | | | | | 120 | | | | | 125 | | | | |
| AAG | AAC | CAG | TAC | CGG | CAT | TAT | TGG | AGT | GAA | AAC | CTT | TTC | CAG | TGC | TTC | 432 |
| Lys | Asn | Gln | Tyr | Arg | His | Tyr | Trp | Ser | Glu | Asn | Leu | Phe | Gln | Cys | Phe | |
| | 130 | | | | | 135 | | | | | 140 | | | | | |
| AAT | TGC | AGC | CTC | TGC | CTC | AAT | GGG | ACC | GTG | CAC | CTC | TCC | TGC | CAG | GAG | 480 |
| Asn | Cys | Ser | Leu | Cys | Leu | Asn | Gly | Thr | Val | His | Leu | Ser | Cys | Gln | Glu | |
| 145 | | | | | 150 | | | | | 155 | | | | | 160 | |
| AAA | CAG | AAC | ACC | GTG | TGC | ACC | | | | | | | | | | 501 |
| Lys | Gln | Asn | Thr | Val | Cys | Thr | | | | | | | | | | |
| | | | | 165 | | | | | | | | | | | | |

( 2 ) INFORMATION FOR SEQ ID NO: 2:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | | |
|---|---|---|---|---|---|---|---|---|---|---|---|---|---|---|---|
| Met | Gly | Leu | Ser | Thr | Val | Pro | Asp | Leu | Leu | Leu | Pro | Leu | Val | Leu | Leu |
| 1 | | | | 5 | | | | | 10 | | | | | 15 | |
| Glu | Leu | Leu | Val | Gly | Ile | Tyr | Pro | Ser | Gly | Val | Ile | Gly | Leu | Val | Pro |
| | | | 20 | | | | | 25 | | | | | 30 | | |
| His | Leu | Gly | Asp | Arg | Glu | Lys | Arg | Asp | Ser | Val | Cys | Pro | Gln | Gly | Lys |
| | | 35 | | | | | 40 | | | | | 45 | | | |
| Tyr | Ile | His | Pro | Gln | Asn | Asn | Ser | Ile | Cys | Cys | Thr | Lys | Cys | His | Lys |
| | 50 | | | | | 55 | | | | | 60 | | | | |
| Gly | Thr | Tyr | Leu | Tyr | Asn | Asp | Cys | Pro | Gly | Pro | Gly | Gln | Asp | Thr | Asp |
| 65 | | | | | 70 | | | | | 75 | | | | | 80 |
| Cys | Arg | Glu | Cys | Glu | Ser | Gly | Ser | Phe | Thr | Ala | Ser | Glu | Asn | His | Leu |
| | | | | 85 | | | | | 90 | | | | | 95 | |
| Arg | His | Cys | Leu | Ser | Cys | Ser | Lys | Cys | Arg | Lys | Glu | Met | Gly | Gln | Val |
| | | | 100 | | | | | 105 | | | | | 110 | | |
| Glu | Ile | Ser | Ser | Cys | Thr | Val | Asp | Arg | Asp | Thr | Val | Cys | Gly | Cys | Arg |
| | | 115 | | | | | 120 | | | | | 125 | | | |

| | | | | | | | | | | | | | | |
|---|---|---|---|---|---|---|---|---|---|---|---|---|---|---|
| Lys | Asn | Gln | Tyr | Arg | His | Tyr | Trp | Ser | Glu | Asn | Leu | Phe | Gln | Cys | Phe |
| | 130 | | | | | 135 | | | | 140 | | | | | |
| Asn | Cys | Ser | Leu | Cys | Leu | Asn | Gly | Thr | Val | His | Leu | Ser | Cys | Gln | Glu |
| 145 | | | | 150 | | | | | 155 | | | | | 160 | |
| Lys | Gln | Asn | Thr | Val | Cys | Thr | | | | | | | | | |
| | | | | 165 | | | | | | | | | | | |

( 2 ) INFORMATION FOR SEQ ID NO: 3:

( i ) SEQUENCE CHARACTERISTICS:
        ( A ) LENGTH: 372 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..372

( x i ) SEQUENCE DESCRIPTION: SEQ ID NO: 3:

| | | | | | | | | | | | | | | | |
|---|---|---|---|---|---|---|---|---|---|---|---|---|---|---|---|
| GTG | TGT | CCC | CAA | GGA | AAA | TAT | ATC | CAC | CCT | CAA | AAT | AAT | TCG | ATT | TGC | 48 |
| Val | Cys | Pro | Gln | Gly | Lys | Tyr | Ile | His | Pro | Gln | Asn | Asn | Ser | Ile | Cys |
| 1 | | | | 5 | | | | | 10 | | | | | 15 | |
| TGT | ACC | AAG | TGC | CAC | AAA | GGA | ACC | TAC | TTG | TAC | AAT | GAC | TGT | CCA | GGC | 96 |
| Cys | Thr | Lys | Cys | His | Lys | Gly | Thr | Tyr | Leu | Tyr | Asn | Asp | Cys | Pro | Gly |
| | | | 20 | | | | | 25 | | | | | 30 | | |
| CCG | GGG | CAG | GAT | ACG | GAC | TGC | AGG | GAG | TGT | GAG | AGC | GGC | TCC | TTC | ACC | 144 |
| Pro | Gly | Gln | Asp | Thr | Asp | Cys | Arg | Glu | Cys | Glu | Ser | Gly | Ser | Phe | Thr |
| | | 35 | | | | | 40 | | | | | 45 | | | |
| GCT | TCA | GAA | AAC | CAC | CTC | AGA | CAC | TGC | CTC | AGC | TGC | TCC | AAA | TGC | CGA | 192 |
| Ala | Ser | Glu | Asn | His | Leu | Arg | His | Cys | Leu | Ser | Cys | Ser | Lys | Cys | Arg |
| | 50 | | | | | 55 | | | | | 60 | | | | |
| AAG | GAA | ATG | GGT | CAG | GTG | GAG | ATC | TCT | TCT | TGC | ACA | GTG | GAC | CGG | GAC | 240 |
| Lys | Glu | Met | Gly | Gln | Val | Glu | Ile | Ser | Ser | Cys | Thr | Val | Asp | Arg | Asp |
| 65 | | | | | 70 | | | | | 75 | | | | | 80 |
| ACC | GTG | TGT | GGC | TGC | AGG | AAG | AAC | CAG | TAC | CGG | CAT | TAT | TGG | AGT | GAA | 288 |
| Thr | Val | Cys | Gly | Cys | Arg | Lys | Asn | Gln | Tyr | Arg | His | Tyr | Trp | Ser | Glu |
| | | | | 85 | | | | | 90 | | | | | 95 | |
| AAC | CTT | TTC | CAG | TGC | TTC | AAT | TGC | AGC | CTC | TGC | CTC | AAT | GGG | ACC | GTG | 336 |
| Asn | Leu | Phe | Gln | Cys | Phe | Asn | Cys | Ser | Leu | Cys | Leu | Asn | Gly | Thr | Val |
| | | | 100 | | | | | 105 | | | | | 110 | | |
| CAC | CTC | TCC | TGC | CAG | GAG | AAA | CAG | AAC | ACC | GTG | TGC | | | | | 372 |
| His | Leu | Ser | Cys | Gln | Glu | Lys | Gln | Asn | Thr | Val | Cys | | | | |
| | | 115 | | | | | 120 | | | | | | | | |

( 2 ) INFORMATION FOR SEQ ID NO: 4:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

| | | | | | | | | | | | | | | | |
|---|---|---|---|---|---|---|---|---|---|---|---|---|---|---|---|
| Val | Cys | Pro | Gln | Gly | Lys | Tyr | Ile | His | Pro | Gln | Asn | Asn | Ser | Ile | Cys |
| 1 | | | | 5 | | | | | 10 | | | | | 15 | |
| Cys | Thr | Lys | Cys | His | Lys | Gly | Thr | Tyr | Leu | Tyr | Asn | Asp | Cys | Pro | Gly |
| | | | 20 | | | | | 25 | | | | | 30 | | |
| Pro | Gly | Gln | Asp | Thr | Asp | Cys | Arg | Glu | Cys | Glu | Ser | Gly | Ser | Phe | Thr |
| | | 35 | | | | | 40 | | | | | 45 | | | |
| Ala | Ser | Glu | Asn | His | Leu | Arg | His | Cys | Leu | Ser | Cys | Ser | Lys | Cys | Arg |

|  | 50 |  |  |  | 55 |  |  |  | 60 |  |  |  |
|---|---|---|---|---|---|---|---|---|---|---|---|---|
| Lys | Glu | Met | Gly | Gln | Val | Glu | Ile | Ser | Ser | Cys | Thr | Val | Asp | Arg | Asp |
| 65 |  |  |  |  | 70 |  |  |  | 75 |  |  |  |  |  | 80 |

Thr Val Cys Gly Cys Arg Lys Asn Gln Tyr Arg His Tyr Trp Ser Glu
                85                          90                         95

Asn Leu Phe Gln Cys Phe Asn Cys Ser Leu Cys Leu Asn Gly Thr Val
               100                         105                      110

His Leu Ser Cys Gln Glu Lys Gln Asn Thr Val Cys
               115                     120

( 2 ) INFORMATION FOR SEQ ID NO: 5:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 5:

Glu Met Gly Gln Val Glu Ile Ser Ser Thr Val Asp Arg Asp Thr Val
 1                   5                          10                         15

Cys Gly ( 2 ) INFORMATION FOR SEQ ID NO: 6:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

AAGGAGATGG GCCAGGTTGA GATCTCTTCT ACTGTTGACA ATGACACTGT GTGTGGC      57

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 7:

GCTGCTCCAA ATGCCGAAAG      20

( 2 ) INFORMATION FOR SEQ ID NO: 8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 8:

AGTTCAAGCT TTTACAGTGC CCTTAACATT CTAA      34

( 2 ) INFORMATION FOR SEQ ID NO: 9:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 9:

Asp Arg Glu Lys Arg
 1               5

( 2 ) INFORMATION FOR SEQ ID NO: 10:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 10:

GTTCTATCGA TAAGAGGCCA TAGCTGTCTG GC          32

( 2 ) INFORMATION FOR SEQ ID NO: 11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 11:

GCTCTCACAC TCTCTCTTCT CCCTGTCCCC TAG          33

( 2 ) INFORMATION FOR SEQ ID NO: 12:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 12:

AGGGAGAAGA GAGAGTGTGA GAGCGGCTCC TTC          33

( 2 ) INFORMATION FOR SEQ ID NO: 13:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 13:

TGCATGGCAG GTACACACGG TGTCCCGGTC CAC          33

( 2 ) INFORMATION FOR SEQ ID NO: 14:

( i ) SEQUENCE CHARACTERISTICS:
    ( A ) LENGTH: 33 base pairs
    ( B ) TYPE: nucleic acid
    ( C ) STRANDEDNESS: single ( D ) TOPOLOGY: linear ( i i ) MOLECULE TYPE: DNA (genomic)

( x i ) SEQUENCE DESCRIPTION: SEQ ID NO: 14:

GACACCGTGT GTACCTGCCA TGCAGGTTTC TTT 33

( 2 ) INFORMATION FOR SEQ ID NO: 15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 15:

GGCCAAGCTT CAGGTGCACA CGGTGTTCTG 30

( 2 ) INFORMATION FOR SEQ ID NO: 16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 16:

GCTGCTCCAA ATGCCGAAAG 20

( 2 ) INFORMATION FOR SEQ ID NO: 17:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 17:

AGTTCAAGCT TTACAGTGCC CTTAACATTC TAA 33

( 2 ) INFORMATION FOR SEQ ID NO: 18:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 18:

CGCAGAATTC CCCGCAGCCA TGGCGCCCGT CGCC 34

( 2 ) INFORMATION FOR SEQ ID NO: 19:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 19:

GTAAGGATCC TATCGCCAGT GCTCCCTTCA GCT    33

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

ACACGACTTC ATCCACGGAT A    21

(2) INFORMATION FOR SEQ ID NO: 21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

ACGTTCTAGA CTAGTCGCCA GTGCTCCCTT CAGCTG    36

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

CAGAACCGCA TCTGCACCTG C    21

(2) INFORMATION FOR SEQ ID NO: 23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

ACGTTCTAGA CTTGCACACC ACGTCTGATG TTTC    34

(2) INFORMATION FOR SEQ ID NO: 24:

(i) SEQUENCE CHARACTERISTICS:
        (A) LENGTH: 2062 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 155..1519

(xi) SEQUENCE DESCRIPTION: SEQ ID NO: 24:

-continued

```
ACCAGTGATC TCTATGCCCG AGTCTCAACC CTCAACTGTC ACCCCAAGGC ACTTGGGACG      60

TCCTGGACAG ACCGAGTCCC GGGAAGCCCC AGCACTGCCG CTGCCACACT GCCCTGAGCC     120

CAAATGGGGG AGTGAGAGGC CATAGCTGTC TGGC ATG GGC CTC TCC ACC GTG         172
                                      Met Gly Leu Ser Thr Val
                                       1               5

CCT GAC CTG CTG CTG CCG CTG GTG CTC CTG GAG CTG TTG GTG GGA ATA      220
Pro Asp Leu Leu Leu Pro Leu Val Leu Leu Glu Leu Leu Val Gly Ile
             10              15                      20

TAC CCC TCA GGG GTT ATT GGA CTG GTC CCT CAC CTA GGG GAC AGG GAG      268
Tyr Pro Ser Gly Val Ile Gly Leu Val Pro His Leu Gly Asp Arg Glu
         25              30                      35

AAG AGA GAT AGT GTG TGT CCC CAA GGA AAA TAT ATC CAC CCT CAA AAT      316
Lys Arg Asp Ser Val Cys Pro Gln Gly Lys Tyr Ile His Pro Gln Asn
     40              45                      50

AAT TCG ATT TGC TGT ACC AAG TGC CAC AAA GGA ACC TAC TTG TAC AAT      364
Asn Ser Ile Cys Cys Thr Lys Cys His Lys Gly Thr Tyr Leu Tyr Asn
 55              60                      65                      70

GAC TGT CCA GGC CCG GGG CAG GAT ACG GAC TGC AGG GAG TGT GAG AGC      412
Asp Cys Pro Gly Pro Gly Gln Asp Thr Asp Cys Arg Glu Cys Glu Ser
                 75              80                      85

GGC TCC TTC ACC GCT TCA GAA AAC CAC CTC AGA CAC TGC CTC AGC TGC      460
Gly Ser Phe Thr Ala Ser Glu Asn His Leu Arg His Cys Leu Ser Cys
             90              95                     100

TCC AAA TGC CGA AAG GAA ATG GGT CAG GTG GAG ATC TCT TCT TGC ACA      508
Ser Lys Cys Arg Lys Glu Met Gly Gln Val Glu Ile Ser Ser Cys Thr
        105             110                     115

GTG GAC CGG GAC ACC GTG TGT GGC TGC AGG AAG AAC CAG TAC CGG CAT      556
Val Asp Arg Asp Thr Val Cys Gly Cys Arg Lys Asn Gln Tyr Arg His
    120             125                     130

TAT TGG AGT GAA AAC CTT TTC CAG TGC TTC AAT TGC AGC CTC TGC CTC      604
Tyr Trp Ser Glu Asn Leu Phe Gln Cys Phe Asn Cys Ser Leu Cys Leu
135             140                     145                     150

AAT GGG ACC GTG CAC CTC TCC TGC CAG GAG AAA CAG AAC ACC GTG TGC      652
Asn Gly Thr Val His Leu Ser Cys Gln Glu Lys Gln Asn Thr Val Cys
                    155             160                     165

ACC TGC CAT GCA GGT TTC TTT CTA AGA GAA AAC GAG TGT GTC TCC TGT      700
Thr Cys His Ala Gly Phe Phe Leu Arg Glu Asn Glu Cys Val Ser Cys
            170             175                     180

AGT AAC TGT AAG AAA AGC CTG GAG TGC ACG AAG TTG TGC CTA CCC CAG      748
Ser Asn Cys Lys Lys Ser Leu Glu Cys Thr Lys Leu Cys Leu Pro Gln
        185             190                     195

ATT GAG AAT GTT AAG GGC ACT GAG GAC TCA GGC ACC ACA GTG CTG TTG      796
Ile Glu Asn Val Lys Gly Thr Glu Asp Ser Gly Thr Thr Val Leu Leu
    200             205                     210

CCC CTG GTC ATT TTC TTT GGT CTT TGC CTT TTA TCC CTC CTC TTC ATT      844
Pro Leu Val Ile Phe Phe Gly Leu Cys Leu Leu Ser Leu Leu Phe Ile
215             220                     225                     230

GGT TTA ATG TAT CGC TAC CAA CGG TGG AAG TCC AAG CTC TAC TCC ATT      892
Gly Leu Met Tyr Arg Tyr Gln Arg Trp Lys Ser Lys Leu Tyr Ser Ile
                    235             240                     245

GTT TGT GGG AAA TCG ACA CCT GAA AAA GAG GGG GAG CTT GAA GGA ACT      940
Val Cys Gly Lys Ser Thr Pro Glu Lys Glu Gly Glu Leu Glu Gly Thr
            250             255                     260

ACT ACT AAG CCC CTG GCC CCA AAC CCA AGC TTC AGT CCC ACT CCA GGC      988
Thr Thr Lys Pro Leu Ala Pro Asn Pro Ser Phe Ser Pro Thr Pro Gly
        265             270                     275

TTC ACC CCC ACC CTG GGC TTC AGT CCC GTG CCC AGT TCC ACC TTC ACC     1036
Phe Thr Pro Thr Leu Gly Phe Ser Pro Val Pro Ser Ser Thr Phe Thr
    280             285                     290
```

| | | | | | | | | | | | | | | | |
|---|---|---|---|---|---|---|---|---|---|---|---|---|---|---|---|
| TCC | AGC | TCC | ACC | TAT | ACC | CCC | GGT | GAC | TGT | CCC | AAC | TTT | GCG | GCT | CCC | 1084
| Ser | Ser | Ser | Thr | Tyr | Thr | Pro | Gly | Asp | Cys | Pro | Asn | Phe | Ala | Ala | Pro |
| 295 | | | | 300 | | | | | 305 | | | | | | 310 |

| CGC | AGA | GAG | GTG | GCA | CCA | CCC | TAT | CAG | GGG | GCT | GAC | CCC | ATC | CTT | GCG | 1132
| Arg | Arg | Glu | Val | Ala | Pro | Pro | Tyr | Gln | Gly | Ala | Asp | Pro | Ile | Leu | Ala |
| | | | | 315 | | | | 320 | | | | | 325 | | |

| ACA | GCC | CTC | GCC | TCC | GAC | CCC | ATC | CCC | AAC | CCC | CTT | CAG | AAG | TGG | GAG | 1180
| Thr | Ala | Leu | Ala | Ser | Asp | Pro | Ile | Pro | Asn | Pro | Leu | Gln | Lys | Trp | Glu |
| | | | 330 | | | | 335 | | | | | 340 | | | |

| GAC | AGT | GCC | CAC | AAG | CCA | CAG | AGC | CTA | GAC | ACT | GAT | GAC | CCC | CGG | ACG | 1228
| Asp | Ser | Ala | His | Lys | Pro | Gln | Ser | Leu | Asp | Thr | Asp | Asp | Pro | Arg | Thr |
| | | 345 | | | | 350 | | | | | 355 | | | | |

| CTG | TAC | GCC | GTG | GTG | GAG | AAC | GTG | CCC | CCG | TTG | CGC | TGG | AAG | GAA | TTC | 1276
| Leu | Tyr | Ala | Val | Val | Glu | Asn | Val | Pro | Pro | Leu | Arg | Trp | Lys | Glu | Phe |
| | 360 | | | | 365 | | | | | 370 | | | | | |

| GTG | CGG | CGC | CTA | GGG | CTG | AGC | GAC | CAC | GAG | ATC | GAT | CGG | CTG | GAG | CTG | 1324
| Val | Arg | Arg | Leu | Gly | Leu | Ser | Asp | His | Glu | Ile | Asp | Arg | Leu | Glu | Leu |
| 375 | | | | | 380 | | | | 385 | | | | | 390 | |

| CAG | AAC | GGG | CGC | TGC | CTG | CGC | GAG | GCG | CAA | TAC | AGC | ATG | CTG | GCG | ACC | 1372
| Gln | Asn | Gly | Arg | Cys | Leu | Arg | Glu | Ala | Gln | Tyr | Ser | Met | Leu | Ala | Thr |
| | | | | 395 | | | | 400 | | | | | 405 | | |

| TGG | AGG | CGG | CGC | ACG | CCG | CGG | CGC | GAG | GCC | ACG | CTG | GAG | CTG | CTG | GGA | 1420
| Trp | Arg | Arg | Arg | Thr | Pro | Arg | Arg | Glu | Ala | Thr | Leu | Glu | Leu | Leu | Gly |
| | | | 410 | | | | 415 | | | | | 420 | | | |

| CGC | GTG | CTC | CGC | GAC | ATG | GAC | CTG | CTG | GGC | TGC | CTG | GAG | GAC | ATC | GAG | 1468
| Arg | Val | Leu | Arg | Asp | Met | Asp | Leu | Leu | Gly | Cys | Leu | Glu | Asp | Ile | Glu |
| | | 425 | | | | 430 | | | | | 435 | | | | |

| GAG | GCG | CTT | TGC | GGC | CCC | GCC | GCG | CTC | CCG | CCC | GCG | CCC | AGT | CTT | CTC | 1516
| Glu | Ala | Leu | Cys | Gly | Pro | Ala | Ala | Leu | Pro | Pro | Ala | Pro | Ser | Leu | Leu |
| | 440 | | | | 445 | | | | | 450 | | | | | |

| AGA | TGAGGCTGCG | CCCTGCGGGC | AGCTCTAAGG | ACCGTCCTCG | CAGATCGCCT | | | | | | | | | | | 1569
| Arg |
| 455 |

| | | | | |
|---|---|---|---|---|
| TCCAACCCCA | CTTTTTTCTG | GAAAGGAGGG | GTCCTGCAGG | GGCAAGCAGG | AGCTAGCAGC | 1629
| CGCCTACTTG | GTGCTAACCC | CTCGATGTAC | ATAGCTTTTC | TCAGCTGCCT | GCGCGCCGCC | 1689
| GACAGTCAGC | GCTGTGCGCG | CGGAGAGAGG | TGCGCCGTGG | GCTCAAGAGC | CTGAGTGGGT | 1749
| GGTTTGCGAG | GATGAGGGAC | GCTATGCCTC | ATGCCGTTT | TGGGTGTCCT | CACCAGCAAG | 1809
| GCTGCTCGGG | GGCCCCTGGT | TCGTCCCTGA | GCCTTTTTCA | CAGTGCATAA | GCAGTTTTTT | 1869
| TTGTTTTTGT | TTGTTTTGT | TTGTTTTTA | AATCAATCAT | GTTACACTAA | TAGAAACTTG | 1929
| GCACTCCTGT | GCCCTCTGCC | TGGACAAGCA | CATAGCAAGC | TGAACTGTCC | TAAGGCAGGG | 1989
| GCGAGCACGG | AACAATGGGG | CCTTCAGCTG | GAGCTGTGGA | CTTTTGTACA | TACACTAAAA | 2049
| TTCTGAAGTT | AAG | | | | | 2062

( 2 ) INFORMATION FOR SEQ ID NO: 25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 25:

| | | | | | | | | | | | | | | |
|---|---|---|---|---|---|---|---|---|---|---|---|---|---|---|
| Met | Gly | Leu | Ser | Thr | Val | Pro | Asp | Leu | Leu | Leu | Pro | Leu | Val | Leu | Leu |
| 1 | | | | 5 | | | | | 10 | | | | | 15 | |

| Glu | Leu | Leu | Val | Gly | Ile | Tyr | Pro | Ser | Gly | Val | Ile | Gly | Leu | Val | Pro |
| | | | 20 | | | | | 25 | | | | | 30 | | |

| | | | | | | | | | | | | | |
|---|---|---|---|---|---|---|---|---|---|---|---|---|---|
|His|Leu|Gly|Asp|Arg|Glu|Lys|Arg|Asp|Ser|Val|Cys|Pro|Gln|Gly|Lys|
| | |35| | | |40| | | |45| | | | |
|Tyr|Ile|His|Pro|Gln|Asn|Asn|Ser|Ile|Cys|Cys|Thr|Lys|Cys|His|Lys|
| |50| | | | |55| | | |60| | | | |
|Gly|Thr|Tyr|Leu|Tyr|Asn|Asp|Cys|Pro|Gly|Pro|Gly|Gln|Asp|Thr|Asp|
|65| | | | |70| | | |75| | | | |80|
|Cys|Arg|Glu|Cys|Glu|Ser|Gly|Ser|Phe|Thr|Ala|Ser|Glu|Asn|His|Leu|
| | | | |85| | | |90| | | | |95| |
|Arg|His|Cys|Leu|Ser|Cys|Ser|Lys|Cys|Arg|Lys|Glu|Met|Gly|Gln|Val|
| | | |100| | | |105| | | |110| | | |
|Glu|Ile|Ser|Ser|Cys|Thr|Val|Asp|Arg|Asp|Thr|Val|Cys|Gly|Cys|Arg|
| | |115| | | |120| | | |125| | | | |
|Lys|Asn|Gln|Tyr|Arg|His|Tyr|Trp|Ser|Glu|Asn|Leu|Phe|Gln|Cys|Phe|
| |130| | | |135| | | | |140| | | | |
|Asn|Cys|Ser|Leu|Cys|Leu|Asn|Gly|Thr|Val|His|Leu|Ser|Cys|Gln|Glu|
|145| | | |150| | | | |155| | | | |160| |
|Lys|Gln|Asn|Thr|Val|Cys|Thr|Cys|His|Ala|Gly|Phe|Phe|Leu|Arg|Glu|
| | | |165| | | |170| | | | |175| | |
|Asn|Glu|Cys|Val|Ser|Cys|Ser|Asn|Cys|Lys|Lys|Ser|Leu|Glu|Cys|Thr|
| | |180| | | | |185| | | |190| | | |
|Lys|Leu|Cys|Leu|Pro|Gln|Ile|Glu|Asn|Val|Lys|Gly|Thr|Glu|Asp|Ser|
| |195| | | | |200| | | |205| | | | |
|Gly|Thr|Thr|Val|Leu|Leu|Pro|Leu|Val|Ile|Phe|Phe|Gly|Leu|Cys|Leu|
|210| | | | |215| | | |220| | | | | |
|Leu|Ser|Leu|Leu|Phe|Ile|Gly|Leu|Met|Tyr|Arg|Tyr|Gln|Arg|Trp|Lys|
|225| | | |230| | | |235| | | | | |240|
|Ser|Lys|Leu|Tyr|Ser|Ile|Val|Cys|Gly|Lys|Ser|Thr|Pro|Glu|Lys|Glu|
| | | |245| | | |250| | | |255| | | |
|Gly|Glu|Leu|Glu|Gly|Thr|Thr|Thr|Lys|Pro|Leu|Ala|Pro|Asn|Pro|Ser|
| | |260| | | |265| | | |270| | | | |
|Phe|Ser|Pro|Thr|Pro|Gly|Phe|Thr|Pro|Thr|Leu|Gly|Phe|Ser|Pro|Val|
| |275| | | |280| | | |285| | | | | |
|Pro|Ser|Ser|Thr|Phe|Thr|Ser|Ser|Ser|Thr|Tyr|Thr|Pro|Gly|Asp|Cys|
|290| | | |295| | | | |300| | | | | |
|Pro|Asn|Phe|Ala|Ala|Pro|Arg|Arg|Glu|Val|Ala|Pro|Pro|Tyr|Gln|Gly|
|305| | | |310| | | |315| | | | |320| |
|Ala|Asp|Pro|Ile|Leu|Ala|Thr|Ala|Leu|Ala|Ser|Asp|Pro|Ile|Pro|Asn|
| | |325| | | |330| | | |335| | | | |
|Pro|Leu|Gln|Lys|Trp|Glu|Asp|Ser|Ala|His|Lys|Pro|Gln|Ser|Leu|Asp|
| |340| | | | |345| | | |350| | | | |
|Thr|Asp|Asp|Pro|Arg|Thr|Leu|Tyr|Ala|Val|Val|Glu|Asn|Val|Pro|Pro|
|355| | | | |360| | | |365| | | | | |
|Leu|Arg|Trp|Lys|Glu|Phe|Val|Arg|Arg|Leu|Gly|Leu|Ser|Asp|His|Glu|
|370| | | |375| | | |380| | | | | | |
|Ile|Asp|Arg|Leu|Glu|Leu|Gln|Asn|Gly|Arg|Cys|Leu|Arg|Glu|Ala|Gln|
|385| | | |390| | | |395| | | | | |400|
|Tyr|Ser|Met|Leu|Ala|Thr|Trp|Arg|Arg|Arg|Thr|Pro|Arg|Arg|Glu|Ala|
| | |405| | | |410| | | | |415| | | |
|Thr|Leu|Glu|Leu|Leu|Gly|Arg|Val|Leu|Arg|Asp|Met|Asp|Leu|Leu|Gly|
|420| | | |425| | | |430| | | | | | |
|Cys|Leu|Glu|Asp|Ile|Glu|Glu|Ala|Leu|Cys|Gly|Pro|Ala|Ala|Leu|Pro|
| |435| | | |440| | | |445| | | | | |
|Pro|Ala|Pro|Ser|Leu|Leu|Arg|
|450| | | | |455| |

( 2 ) INFORMATION FOR SEQ ID NO: 26:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 26:

```
Val Cys Pro Gln Gly Lys Tyr Ile His Pro Gln Asn Asn Ser Ile Cys
 1               5                  10                  15
Cys Thr Lys Cys His Lys Gly Thr Tyr Leu Tyr Asn Asp Cys Pro Gly
            20                  25                  30
Pro Gly Gln Asp Thr Asp Cys Arg
        35                  40
```

( 2 ) INFORMATION FOR SEQ ID NO: 27:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 27:

```
Thr Cys Arg Leu Arg Glu Tyr Tyr Asp Gln Thr Ala Gln Met Cys Cys
 1               5                  10                  15
Ser Lys Cys Ser Pro Gly Gln His Ala Lys Val Phe Cys Thr Lys Thr
            20                  25                  30
Ser Asp Thr Val Cys Asp
        35
```

( 2 ) INFORMATION FOR SEQ ID NO: 28:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 28:

```
Thr Cys Ser Thr Gly Leu Tyr Thr His Ser Gly Glu Cys Cys Lys Ala
 1               5                  10                  15
Cys Asn Leu Gly Glu Gly Val Ala Gln Pro Cys Gly Ala Asn Gln Thr
            20                  25                  30
Val Cys Glu
        35
```

( 2 ) INFORMATION FOR SEQ ID NO: 29:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 29:

-continued

```
Ala  Cys  Arg  Glu  Lys  Gln  Tyr  Leu  Ile  Asn  Ser  Gln  Cys  Cys  Ser  Leu
 1              5                        10                       15

Cys  Gln  Pro  Gly  Gln  Lys  Leu  Val  Ser  Asp  Cys  Thr  Glu  Phe  Thr  Glu
              20                       25                       30

Thr  Glu  Cys  Leu
          35
```

(2) INFORMATION FOR SEQ ID NO: 30:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 30:

```
Asn  Cys  Val  Lys  Asp  Thr  Tyr  Pro  Ser  Gly  His  Lys  Cys  Cys  Arg  Glu
 1              5                        10                       15

Cys  Gln  Pro  Gly  His  Gly  Met  Val  Ser  Arg  Cys  Asp  His  Thr  Arg  Asp
              20                       25                       30

Thr  Val  Cys  His
          35
```

(2) INFORMATION FOR SEQ ID NO: 31:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 31:

```
Glu  Cys  Glu  Ser  Gly  Ser  Phe  Thr  Ala  Ser  Glu  Asn  His  Leu  Arg  His
 1              5                        10                       15

Cys  Leu  Ser  Cys  Ser  Lys  Cys  Arg  Lys  Glu  Met  Gly  Gln  Val  Glu  Ile
              20                       25                       30

Ser  Ser  Cys  Thr  Val  Asp  Arg  Asp  Thr  Val  Cys
          35                       40
```

(2) INFORMATION FOR SEQ ID NO: 32:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

```
Ser  Cys  Glu  Asp  Ser  Thr  Tyr  Thr  Gln  Leu  Trp  Asn  Trp  Val  Pro  Glu
 1              5                        10                       15

Cys  Leu  Ser  Cys  Gly  Ser  Arg  Cys  Ser  Ser  Asp  Gln  Val  Glu  Thr  Gln
              20                       25                       30

Ala  Cys  Thr  Arg  Glu  Gln  Asn  Arg  Ile  Cys
          35                       40
```

(2) INFORMATION FOR SEQ ID NO: 33:

(i) SEQUENCE CHARACTERISTICS:
        (A) LENGTH: 42 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO: 33:

```
Pro Cys Leu Asp Asn Val Thr Phe Ser Asp Val Val Ser Ala Thr Glu
 1               5                  10                  15
Pro Cys Lys Pro Cys Thr Glu Cys Leu Gly Leu Gln Ser Met Ser Ala
            20                  25                  30
Pro Cys Val Glu Ala Asp Asp Ala Val Cys
            35                  40
```

(2) INFORMATION FOR SEQ ID NO: 34:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 34:

```
Pro Cys Gly Glu Ser Glu Phe Leu Asp Thr Trp Asn Arg Glu Thr His
 1               5                  10                  15
Cys His Gln His Lys Tyr Cys Asp Pro Asn Leu Gly Leu Arg Val Gln
            20                  25                  30
Gln Lys Gly Thr Ser Glu Thr Asp Thr Ile Cys
            35                  40
```

(2) INFORMATION FOR SEQ ID NO: 35:

(i) SEQUENCE CHARACTERISTICS:
(A) LENGTH: 42 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 35:

```
Pro Cys Glu Pro Gly Phe Tyr Asn Glu Ala Val Asn Tyr Asp Thr Cys
 1               5                  10                  15
Lys Gln Cys Thr Gln Cys Asn His Arg Ser Gly Ser Glu Leu Lys Gln
            20                  25                  30
Asn Cys Thr Pro Thr Glu Asp Thr Val Cys
            35                  40
```

(2) INFORMATION FOR SEQ ID NO: 36:

(i) SEQUENCE CHARACTERISTICS:
(A) LENGTH: 41 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 36:

```
Gly Cys Arg Lys Asn Gln Tyr Arg His Tyr Trp Ser Glu Asn Leu Phe
 1               5                  10                  15
Gln Cys Phe Asn Cys Ser Leu Cys Leu Asn Gly Thr Val His Leu Ser
            20                  25                  30
```

Cys Gln Glu Lys Gln Asn Thr Val Cys
                         35                          40

( 2 ) INFORMATION FOR SEQ ID NO: 37:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 37:

Thr Cys Arg Pro Gly Trp Tyr Cys Ala Leu Ser Lys Gln Glu Gly Cys
        1               5                   10                  15

Arg Leu Cys Ala Pro Leu Arg Lys Cys Arg Pro Gly Phe Gly Val Ala
                        20                  25                  30

Arg Pro Gly Thr Glu Thr Ser Asp Val Val Cys Lys
                        35                  40

( 2 ) INFORMATION FOR SEQ ID NO: 38:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 38:

Arg Cys Ala Tyr Gly Tyr Tyr Gln Asp Glu Glu Thr Gly His Cys Glu
        1               5                   10                  15

Ala Cys Ser Val Cys Glu Val Gly Ser Gly Leu Val Phe Ser Cys Gln
                        20                  25                  30

Asp Lys Gln Asn Thr Val Cys Glu
                        35                  40

( 2 ) INFORMATION FOR SEQ ID NO: 39:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 39:

Thr Cys Glu Glu Gly Trp His Cys Thr Ser Glu Ala Cys Glu Ser Cys
        1               5                   10                  15

Val Leu His Arg Ser Cys Ser Pro Gly Phe Gly Val Lys Gln Ile Ala
                        20                  25                  30

Thr Gly Val Ser Asp Thr Ile Cys Glu
                        35                  40

( 2 ) INFORMATION FOR SEQ ID NO: 40:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 40:

Thr Cys His Ala Gly Phe Phe Leu Arg Glu Asn Glu Cys Val Ser Cys
1               5                   10                  15

Ser Asn Cys Lys Lys Ser Leu Glu Cys Thr Lys Leu Cys Leu Pro Gln
            20                  25                  30

Ile Glu Asn Val Lys Gly Thr
            35

( 2 ) INFORMATION FOR SEQ ID NO: 41:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 41:

Pro Cys Ala Pro Gly Thr Phe Ser Asn Thr Thr Ser Ser Thr Asp Ile
1               5                   10                  15

Cys Arg Pro His Gln Ile Cys Asn Val Val Ala Ile Pro Gly Asn Ala
            20                  25                  30

Ser Met Asp Ala Val Cys Thr
            35

( 2 ) INFORMATION FOR SEQ ID NO: 42:

( i ) SEQUENCE CHARACTERISTICS:
( A ) LENGTH: 42 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 42:

Glu Cys Pro Glu Gly Thr Tyr Ser Asp Glu Ala Asn His Val Asp Pro
1               5                   10                  15

Cys Leu Pro Cys Thr Val Cys Glu Asp Thr Glu Arg Gln Leu Arg Glu
            20                  25                  30

Cys Thr Pro Trp Ala Asp Ala Glu Cys Glu
            35                  40

( 2 ) INFORMATION FOR SEQ ID NO: 43:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 43:

Pro Cys Pro Val Gly Phe Phe Ser Asn Val Ser Ser Ala Phe Glu Lys
1               5                   10                  15

Cys His Pro Trp Thr Ser Cys Glu Thr Lys Asp Leu Val Val Gln Gln
            20                  25                  30

Ala Gly Thr Asn Lys Thr Asp Val Val Cys Gly
            35                  40

( 2 ) INFORMATION FOR SEQ ID NO: 44:

( i ) SEQUENCE CHARACTERISTICS:
   ( A ) LENGTH: 41 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO: 44:

```
Pro Cys Pro Pro Gly His Phe Ser Pro Gly Ser Asn Gln Ala Cys Lys
 1               5                  10                      15

Pro Trp Thr Asn Cys Thr Leu Ser Gly Lys Gln Ile Arg His Pro Ala
             20                  25                  30

Ser Asn Ser Leu Asp Thr Val Cys Glu
         35                  40
```

( 2 ) INFORMATION FOR SEQ ID NO: 45:

( i ) SEQUENCE CHARACTERISTICS:
      ( A ) LENGTH: 12 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO: 45:

TGTCTGGCAT GG                                                    12

( 2 ) INFORMATION FOR SEQ ID NO: 46:

( i ) SEQUENCE CHARACTERISTICS:
      ( A ) LENGTH: 12 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO: 46:

CCCCAGATTT AG                                                    12

( 2 ) INFORMATION FOR SEQ ID NO: 47:

( i ) SEQUENCE CHARACTERISTICS:
      ( A ) LENGTH: 600 base pairs
      ( B ) TYPE: nucleic acid
      ( C ) STRANDEDNESS: double
      ( D ) TOPOLOGY: linear ( i i ) MOLECULE TYPE: cDNA to mRNA ( i x ) FEATURE:
      ( A ) NAME/KEY: CDS
      ( B ) LOCATION: 1..597

( x i ) SEQUENCE DESCRIPTION: SEQ ID NO: 47:

```
ATG GGC CTC TCC ACC GTG CCT GAC CTG CTG CTG CCG CTG GTG CTC CTG     48
Met Gly Leu Ser Thr Val Pro Asp Leu Leu Leu Pro Leu Val Leu Leu
 1               5                  10                      15

GAG CTG TTG GTG GGA ATA TAC CCC TCA GGG GTT ATT GGA CTG GTC CCT     96
Glu Leu Leu Val Gly Ile Tyr Pro Ser Gly Val Ile Gly Leu Val Pro
             20                  25                  30

CAC CTA GGG GAC AGG GAG AAG AGA GAT AGT GTG TGT CCC ACA GGA AAA    144
His Leu Gly Asp Arg Glu Lys Arg Asp Ser Val Cys Pro Thr Gly Lys
         35                  40                  45

TAT ATC CAC CCT CAA AAT AAT TCG ATT TGC TGT ACC AAG TGC CAC AAA    192
Tyr Ile His Pro Gln Asn Asn Ser Ile Cys Cys Thr Lys Cys His Lys
```

```
                  50                           55                           60
GGA  ACC  TAC  TTG  TAC  AAT  GAC  TGT  CCA  GGC  CCG  GGG  CAG  GAT  ACG  GAC      240
Gly  Thr  Tyr  Leu  Tyr  Asn  Asp  Cys  Pro  Gly  Pro  Gly  Gln  Asp  Thr  Asp
 65                      70                        75                       80

TGC  AGG  GAG  TGT  GAG  AGC  GGC  TCC  TTC  ACC  GCT  TCA  GAA  AAC  CAC  CTC      288
Cys  Arg  Glu  Cys  Glu  Ser  Gly  Ser  Phe  Thr  Ala  Ser  Glu  Asn  His  Leu
                    85                          90                    95

AGA  CAC  TGC  CTC  AGC  TGC  TCC  AAA  TGC  CGA  AAG  GAA  ATG  GGT  CAG  GTG      336
Arg  His  Cys  Leu  Ser  Cys  Ser  Lys  Cys  Arg  Lys  Glu  Met  Gly  Gln  Val
               100                           105                 110

GAG  ATC  TCT  TCT  TGC  ACA  GTG  GAC  CGG  GAC  ACC  GTG  TGT  GGC  TGC  AGG      384
Glu  Ile  Ser  Ser  Cys  Thr  Val  Asp  Arg  Asp  Thr  Val  Cys  Gly  Cys  Arg
          115                     120                     125

AAG  AAC  CAG  TAC  CGG  CAT  TAT  TGG  AGT  GAA  AAC  CTT  TTC  CAG  TGC  TTC      432
Lys  Asn  Gln  Tyr  Arg  His  Tyr  Trp  Ser  Glu  Asn  Leu  Phe  Gln  Cys  Phe
130                          135                          140

AAT  TGC  AGC  CTC  TGC  CTC  AAT  GGG  ACC  GTG  CAC  CTC  TCC  TGC  CAG  GAG      480
Asn  Cys  Ser  Leu  Cys  Leu  Asn  Gly  Thr  Val  His  Leu  Ser  Cys  Gln  Glu
145                          150                     155                      160

AAA  CAG  AAC  ACC  GTG  TGC  ACC  TGC  CAT  GCA  GGT  TTC  TTT  CTA  AGA  GAA      528
Lys  Gln  Asn  Thr  Val  Cys  Thr  Cys  His  Ala  Gly  Phe  Phe  Leu  Arg  Glu
                    165                     170                     175

AAC  GAG  TGT  GTC  TCC  TGT  AGT  AAC  TGT  AAG  AAA  AGC  CTG  GAG  TGC  ACG      576
Asn  Glu  Cys  Val  Ser  Cys  Ser  Asn  Cys  Lys  Lys  Ser  Leu  Glu  Cys  Thr
               180                     185                     190

AAG  TTG  TGC  CTA  CCC  CAG  ATT  TAG                                              600
Lys  Leu  Cys  Leu  Pro  Gln  Ile
               195                   200
```

( 2 ) INFORMATION FOR SEQ ID NO: 48:

( i ) SEQUENCE CHARACTERISTICS:
        ( A ) LENGTH: 199 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 48:

```
Met  Gly  Leu  Ser  Thr  Val  Pro  Asp  Leu  Leu  Leu  Pro  Leu  Val  Leu  Leu
 1                      5                        10                       15

Glu  Leu  Leu  Val  Gly  Ile  Tyr  Pro  Ser  Gly  Val  Ile  Gly  Leu  Val  Pro
                    20                      25                      30

His  Leu  Gly  Asp  Arg  Glu  Lys  Arg  Asp  Ser  Val  Cys  Pro  Thr  Gly  Lys
               35                           40                  45

Tyr  Ile  His  Pro  Gln  Asn  Asn  Ser  Ile  Cys  Cys  Thr  Lys  Cys  His  Lys
     50                           55                            60

Gly  Thr  Tyr  Leu  Tyr  Asn  Asp  Cys  Pro  Gly  Pro  Gly  Gln  Asp  Thr  Asp
 65                      70                       75                       80

Cys  Arg  Glu  Cys  Glu  Ser  Gly  Ser  Phe  Thr  Ala  Ser  Glu  Asn  His  Leu
                    85                      90                      95

Arg  His  Cys  Leu  Ser  Cys  Ser  Lys  Cys  Arg  Lys  Glu  Met  Gly  Gln  Val
               100                          105                 110

Glu  Ile  Ser  Ser  Cys  Thr  Val  Asp  Arg  Asp  Thr  Val  Cys  Gly  Cys  Arg
          115                     120                     125

Lys  Asn  Gln  Tyr  Arg  His  Tyr  Trp  Ser  Glu  Asn  Leu  Phe  Gln  Cys  Phe
130                          135                          140

Asn  Cys  Ser  Leu  Cys  Leu  Asn  Gly  Thr  Val  His  Leu  Ser  Cys  Gln  Glu
145                          150                     155                      160
```

| Lys | Gln | Asn | Thr | Val | Cys | Thr | Cys | His | Ala | Gly | Phe | Phe | Leu | Arg | Glu |
|     |     |     |     | 165 |     |     |     | 170 |     |     |     |     |     | 175 |     |

| Asn | Glu | Cys | Val | Ser | Cys | Ser | Asn | Cys | Lys | Lys | Ser | Leu | Glu | Cys | Thr |
|     |     |     | 180 |     |     |     |     | 185 |     |     |     |     | 190 |     |     |

| Lys | Leu | Cys | Leu | Pro | Gln | Ile |
|     |     | 195 |     |     |     |     |

( 2 ) INFORMATION FOR SEQ ID NO: 49:

( i ) SEQUENCE CHARACTERISTICS:
        ( A ) LENGTH: 474 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..471

( x i ) SEQUENCE DESCRIPTION: SEQ ID NO: 49:

| ATG | GGC | CTC | TCC | ACC | GTG | CCT | GAC | CTG | CTG | CTG | CCG | CTG | GTG | CTC | CTG | 48 |
| Met | Gly | Leu | Ser | Thr | Val | Pro | Asp | Leu | Leu | Leu | Pro | Leu | Val | Leu | Leu |    |
| 1   |     |     |     | 5   |     |     |     |     | 10  |     |     |     |     | 15  |     |    |

| GAG | CTG | TTG | GTG | GGA | ATA | TAC | CCC | TCA | GGG | GTT | ATT | GGA | CTG | GTC | CCT | 96 |
| Glu | Leu | Leu | Val | Gly | Ile | Tyr | Pro | Ser | Gly | Val | Ile | Gly | Leu | Val | Pro |    |
|     |     |     | 20  |     |     |     |     | 25  |     |     |     |     | 30  |     |     |    |

| CAC | CTA | GGG | GAC | AGG | GAG | AAG | AGA | GAG | TGT | GAG | AGC | GGC | TCC | TTC | ACC | 144 |
| His | Leu | Gly | Asp | Arg | Glu | Lys | Arg | Glu | Cys | Glu | Ser | Gly | Ser | Phe | Thr |     |
|     |     | 35  |     |     |     |     | 40  |     |     |     |     | 45  |     |     |     |     |

| GCT | TCA | GAA | AAC | CAC | CTC | AGA | CAC | TGC | CTC | AGC | TGC | TCC | AAA | TGC | CGA | 192 |
| Ala | Ser | Glu | Asn | His | Leu | Arg | His | Cys | Leu | Ser | Cys | Ser | Lys | Cys | Arg |     |
|     | 50  |     |     |     |     | 55  |     |     |     |     | 60  |     |     |     |     |     |

| AAG | GAA | ATG | GGT | CAG | GTG | GAG | ATC | TCT | TCT | TGC | ACA | GTG | GAC | CGG | GAC | 240 |
| Lys | Glu | Met | Gly | Gln | Val | Glu | Ile | Ser | Ser | Cys | Thr | Val | Asp | Arg | Asp |     |
| 65  |     |     |     |     | 70  |     |     |     |     | 75  |     |     |     |     | 80  |     |

| ACC | GTG | TGT | GGC | TGC | AGG | AAG | AAC | CAG | TAC | CGG | CAT | TAT | TGG | AGT | GAA | 288 |
| Thr | Val | Cys | Gly | Cys | Arg | Lys | Asn | Gln | Tyr | Arg | His | Tyr | Trp | Ser | Glu |     |
|     |     |     |     | 85  |     |     |     |     | 90  |     |     |     |     | 95  |     |     |

| AAC | CTT | TTC | CAG | TGC | TTC | AAT | TGC | AGC | CTC | TGC | CTC | AAT | GGG | ACC | GTG | 336 |
| Asn | Leu | Phe | Gln | Cys | Phe | Asn | Cys | Ser | Leu | Cys | Leu | Asn | Gly | Thr | Val |     |
|     |     |     | 100 |     |     |     |     | 105 |     |     |     |     | 110 |     |     |     |

| CAC | CTC | TCC | TGC | CAG | GAG | AAA | CAG | AAC | ACC | GTG | TGC | ACC | TGC | CAT | GCA | 384 |
| His | Leu | Ser | Cys | Gln | Glu | Lys | Gln | Asn | Thr | Val | Cys | Thr | Cys | His | Ala |     |
|     |     | 115 |     |     |     |     | 120 |     |     |     |     | 125 |     |     |     |     |

| GGT | TTC | TTT | CTA | AGA | GAA | AAC | GAG | TGT | GTC | TCC | TGT | AGT | AAC | TGT | AAG | 432 |
| Gly | Phe | Phe | Leu | Arg | Glu | Asn | Glu | Cys | Val | Ser | Cys | Ser | Asn | Cys | Lys |     |
|     | 130 |     |     |     |     | 135 |     |     |     |     | 140 |     |     |     |     |     |

| AAA | AGC | CTG | GAG | TGC | ACG | AAG | TTG | TGC | CTA | CCC | CAG | ATT | TAG | 474 |
| Lys | Ser | Leu | Glu | Cys | Thr | Lys | Leu | Cys | Leu | Pro | Gln | Ile |     |     |
| 145 |     |     |     | 150 |     |     |     |     | 155 |     |     |     |     |     |

( 2 ) INFORMATION FOR SEQ ID NO: 50:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 50:

| Met | Gly | Leu | Ser | Thr | Val | Pro | Asp | Leu | Leu | Leu | Pro | Leu | Val | Leu | Leu |
| 1   |     |     |     | 5   |     |     |     |     | 10  |     |     |     |     | 15  |     |

```
Glu  Leu  Leu  Val  Gly  Ile  Tyr  Pro  Ser  Gly  Val  Ile  Gly  Leu  Val  Pro
               20                       25                      30

His  Leu  Gly  Asp  Arg  Glu  Lys  Arg  Glu  Cys  Glu  Ser  Gly  Ser  Phe  Thr
               35                       40                      45

Ala  Ser  Glu  Asn  His  Leu  Arg  His  Cys  Leu  Ser  Cys  Ser  Lys  Cys  Arg
          50                       55                      60

Lys  Glu  Met  Gly  Gln  Val  Glu  Ile  Ser  Ser  Cys  Thr  Val  Asp  Arg  Asp
65                       70                      75                           80

Thr  Val  Cys  Gly  Cys  Arg  Lys  Asn  Gln  Tyr  Arg  His  Tyr  Trp  Ser  Glu
                    85                       90                      95

Asn  Leu  Phe  Gln  Cys  Phe  Asn  Cys  Ser  Leu  Cys  Leu  Asn  Gly  Thr  Val
               100                      105                     110

His  Leu  Ser  Cys  Gln  Glu  Lys  Gln  Asn  Thr  Val  Cys  Thr  Cys  His  Ala
               115                      120                     125

Gly  Phe  Phe  Leu  Arg  Glu  Asn  Glu  Cys  Val  Ser  Cys  Ser  Asn  Cys  Lys
     130                      135                     140

Lys  Ser  Leu  Glu  Cys  Thr  Lys  Leu  Cys  Leu  Pro  Gln  Ile
145                      150                     155
```

( 2 ) INFORMATION FOR SEQ ID NO: 51:

( i ) SEQUENCE CHARACTERISTICS:
        ( A ) LENGTH: 462 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..459

( x i ) SEQUENCE DESCRIPTION: SEQ ID NO: 51:

```
ATG  GGC  CTC  TCC  ACC  GTG  CCT  GAC  CTG  CTG  CTG  CCG  CTG  GTG  CTC  CTG     48
Met  Gly  Leu  Ser  Thr  Val  Pro  Asp  Leu  Leu  Leu  Pro  Leu  Val  Leu  Leu
1              5                        10                      15

GAG  CTG  TTG  GTG  GGA  ATA  TAC  CCC  TCA  GGG  GTT  ATT  GGA  CTG  GTC  CCT     96
Glu  Leu  Leu  Val  Gly  Ile  Tyr  Pro  Ser  Gly  Val  Ile  Gly  Leu  Val  Pro
               20                       25                      30

CAC  CTA  GGG  GAC  AGG  GAG  AAG  AGA  GAT  AGT  GTG  TGT  CCC  CAA  GGA  AAA    144
His  Leu  Gly  Asp  Arg  Glu  Lys  Arg  Asp  Ser  Val  Cys  Pro  Gln  Gly  Lys
               35                       40                      45

TAT  ATC  CAC  CCT  CAA  AAT  AAT  TCG  ATT  TGC  TGT  ACC  AAG  TGC  CAC  AAA    192
Tyr  Ile  His  Pro  Gln  Asn  Asn  Ser  Ile  Cys  Cys  Thr  Lys  Cys  His  Lys
          50                       55                      60

GGA  ACC  TAC  TTG  TAC  AAT  GAC  TGT  CCA  GGC  CCG  GGG  CAG  GAT  ACG  GAC    240
Gly  Thr  Tyr  Leu  Tyr  Asn  Asp  Cys  Pro  Gly  Pro  Gly  Gln  Asp  Thr  Asp
65                       70                      75                           80

TGC  AGG  AAG  AAC  CAG  TAC  CGG  CAT  TAT  TGG  AGT  GAA  AAC  CTT  TTC  CAG    288
Cys  Arg  Lys  Asn  Gln  Tyr  Arg  His  Tyr  Trp  Ser  Glu  Asn  Leu  Phe  Gln
                    85                       90                      95

TGC  TTC  AAT  TGC  AGC  CTC  TGC  CTC  AAT  GGG  ACC  GTG  CAC  CTC  TCC  TGC    336
Cys  Phe  Asn  Cys  Ser  Leu  Cys  Leu  Asn  Gly  Thr  Val  His  Leu  Ser  Cys
               100                      105                     110

CAG  GAG  AAA  CAG  AAC  ACC  GTG  TGC  ACC  TGC  CAT  GCA  GGT  TTC  TTT  CTA    384
Gln  Glu  Lys  Gln  Asn  Thr  Val  Cys  Thr  Cys  His  Ala  Gly  Phe  Phe  Leu
               115                      120                     125

AGA  GAA  AAC  GAG  TGT  GTC  TCC  TGT  AGT  AAC  TGT  AAG  AAA  AGC  CTG  GAG    432
Arg  Glu  Asn  Glu  Cys  Val  Ser  Cys  Ser  Asn  Cys  Lys  Lys  Ser  Leu  Glu
     130                      135                     140
```

```
TGC  ACG  AAG  TTG  TGC  CTA  CCC  CAG  ATT  TAG                                          462
Cys  Thr  Lys  Leu  Cys  Leu  Pro  Gln  Ile
145                      150
```

( 2 ) INFORMATION FOR SEQ ID NO: 52:

( i ) SEQUENCE CHARACTERISTICS:
        ( A ) LENGTH: 153 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 52:

```
Met  Gly  Leu  Ser  Thr  Val  Pro  Asp  Leu  Leu  Pro  Leu  Val  Leu  Leu
1                   5                        10                      15

Glu  Leu  Leu  Val  Gly  Ile  Tyr  Pro  Ser  Gly  Val  Ile  Gly  Leu  Val  Pro
               20                       25                      30

His  Leu  Gly  Asp  Arg  Glu  Lys  Arg  Asp  Ser  Val  Cys  Pro  Gln  Gly  Lys
               35                       40                      45

Tyr  Ile  His  Pro  Gln  Asn  Asn  Ser  Ile  Cys  Cys  Thr  Lys  Cys  His  Lys
          50                       55                      60

Gly  Thr  Tyr  Leu  Tyr  Asn  Asp  Cys  Pro  Gly  Pro  Gly  Gln  Asp  Thr  Asp
65                       70                      75                           80

Cys  Arg  Lys  Asn  Gln  Tyr  Arg  His  Tyr  Trp  Ser  Glu  Asn  Leu  Phe  Gln
                    85                       90                       95

Cys  Phe  Asn  Cys  Ser  Leu  Cys  Leu  Asn  Gly  Thr  Val  His  Leu  Ser  Cys
               100                      105                     110

Gln  Glu  Lys  Gln  Asn  Thr  Val  Cys  Thr  Cys  His  Ala  Gly  Phe  Phe  Leu
          115                      120                     125

Arg  Glu  Asn  Glu  Cys  Val  Ser  Cys  Ser  Asn  Cys  Lys  Lys  Ser  Leu  Glu
     130                      135                     140

Cys  Thr  Lys  Leu  Cys  Leu  Pro  Gln  Ile
145                      150
```

( 2 ) INFORMATION FOR SEQ ID NO: 53:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..474

( x i ) SEQUENCE DESCRIPTION: SEQ ID NO: 53:

```
ATG  GGC  CTC  TCC  ACC  GTG  CCT  GAC  CTG  CTG  CTG  CCG  CTG  GTG  CTC  CTG     48
Met  Gly  Leu  Ser  Thr  Val  Pro  Asp  Leu  Leu  Leu  Pro  Leu  Val  Leu  Leu
1                   5                        10                      15

GAG  CTG  TTG  GTG  GGA  ATA  TAC  CCC  TCA  GGG  GTT  ATT  GGA  CTG  GTC  CCT     96
Glu  Leu  Leu  Val  Gly  Ile  Tyr  Pro  Ser  Gly  Val  Ile  Gly  Leu  Val  Pro
               20                       25                      30

CAC  CTA  GGG  GAC  AGG  GAG  AAG  AGA  GAT  AGT  GTG  TGT  CCC  CAA  GGA  AAA    144
His  Leu  Gly  Asp  Arg  Glu  Lys  Arg  Asp  Ser  Val  Cys  Pro  Gln  Gly  Lys
               35                       40                      45

TAT  ATC  CAC  CCT  CAA  AAT  AAT  TCG  ATT  TGC  TGT  ACC  AAG  TGC  CAC  AAA    192
Tyr  Ile  His  Pro  Gln  Asn  Asn  Ser  Ile  Cys  Cys  Thr  Lys  Cys  His  Lys
          50                       55                      60
```

| | | | | | | | | | | | | | | | |
|---|---|---|---|---|---|---|---|---|---|---|---|---|---|---|---|
| GGA | ACC | TAC | TTG | TAC | AAT | GAC | TGT | CCA | GGC | CCG | GGG | CAG | GAT | ACG | GAC | 240
| Gly | Thr | Tyr | Leu | Tyr | Asn | Asp | Cys | Pro | Gly | Pro | Gly | Gln | Asp | Thr | Asp |
| 65 | | | | 70 | | | | | 75 | | | | | | 80 |
| TGC | AGG | GAG | TGT | GAG | AGC | GGC | TCC | TTC | ACC | GCT | TCA | GAA | AAC | CAC | CTC | 288
| Cys | Arg | Glu | Cys | Glu | Ser | Gly | Ser | Phe | Thr | Ala | Ser | Glu | Asn | His | Leu |
| | | | | 85 | | | | | 90 | | | | | 95 | |
| AGA | CAC | TGC | CTC | AGC | TGC | TCC | AAA | TGC | CGA | AAG | GAA | ATG | GGT | CAG | GTG | 336
| Arg | His | Cys | Leu | Ser | Cys | Ser | Lys | Cys | Arg | Lys | Glu | Met | Gly | Gln | Val |
| | | | 100 | | | | | 105 | | | | | 110 | | |
| GAG | ATC | TCT | TCT | TGC | ACA | GTG | GAC | CGG | GAC | ACC | GTG | TGT | ACC | TGC | CAT | 384
| Glu | Ile | Ser | Ser | Cys | Thr | Val | Asp | Arg | Asp | Thr | Val | Cys | Thr | Cys | His |
| | | 115 | | | | | 120 | | | | | 125 | | | |
| GCA | GGT | TTC | TTT | CTA | AGA | GAA | AAC | GAG | TGT | GTC | TCC | TGT | AGT | AAC | TGT | 432
| Ala | Gly | Phe | Phe | Leu | Arg | Glu | Asn | Glu | Cys | Val | Ser | Cys | Ser | Asn | Cys |
| | 130 | | | | | 135 | | | | | 140 | | | | |
| AAG | AAA | AGC | CTG | GAG | TGC | ACG | AAG | TTG | TGC | CTA | CCC | CAG | ATT | TAG | | 477
| Lys | Lys | Ser | Leu | Glu | Cys | Thr | Lys | Leu | Cys | Leu | Pro | Gln | Ile | | |
| 145 | | | | | 150 | | | | | 155 | | | | | |

( 2 ) INFORMATION FOR SEQ ID NO: 54:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 54:

| | | | | | | | | | | | | | | | |
|---|---|---|---|---|---|---|---|---|---|---|---|---|---|---|---|
| Met | Gly | Leu | Ser | Thr | Val | Pro | Asp | Leu | Leu | Leu | Pro | Leu | Val | Leu | Leu |
| 1 | | | | 5 | | | | | 10 | | | | | 15 | |
| Glu | Leu | Leu | Val | Gly | Ile | Tyr | Pro | Ser | Gly | Val | Ile | Gly | Leu | Val | Pro |
| | | | 20 | | | | | 25 | | | | | 30 | | |
| His | Leu | Gly | Asp | Arg | Glu | Lys | Arg | Asp | Ser | Val | Cys | Pro | Gln | Gly | Lys |
| | | 35 | | | | | 40 | | | | | 45 | | | |
| Tyr | Ile | His | Pro | Gln | Asn | Asn | Ser | Ile | Cys | Cys | Thr | Lys | Cys | His | Lys |
| | 50 | | | | | 55 | | | | | 60 | | | | |
| Gly | Thr | Tyr | Leu | Tyr | Asn | Asp | Cys | Pro | Gly | Pro | Gly | Gln | Asp | Thr | Asp |
| 65 | | | | | 70 | | | | | 75 | | | | | 80 |
| Cys | Arg | Glu | Cys | Glu | Ser | Gly | Ser | Phe | Thr | Ala | Ser | Glu | Asn | His | Leu |
| | | | | 85 | | | | | 90 | | | | | 95 | |
| Arg | His | Cys | Leu | Ser | Cys | Ser | Lys | Cys | Arg | Lys | Glu | Met | Gly | Gln | Val |
| | | | 100 | | | | | 105 | | | | | 110 | | |
| Glu | Ile | Ser | Ser | Cys | Thr | Val | Asp | Arg | Asp | Thr | Val | Cys | Thr | Cys | His |
| | | 115 | | | | | 120 | | | | | 125 | | | |
| Ala | Gly | Phe | Phe | Leu | Arg | Glu | Asn | Glu | Cys | Val | Ser | Cys | Ser | Asn | Cys |
| | 130 | | | | | 135 | | | | | 140 | | | | |
| Lys | Lys | Ser | Leu | Glu | Cys | Thr | Lys | Leu | Cys | Leu | Pro | Gln | Ile | | |
| 145 | | | | | 150 | | | | | 155 | | | | | |

( 2 ) INFORMATION FOR SEQ ID NO: 55:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 55:

GTGTGCACCT GA                                      12

( 2 ) INFORMATION FOR SEQ ID NO: 56:

( i ) SEQUENCE CHARACTERISTICS:
        ( A ) LENGTH: 504 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..501

( x i ) SEQUENCE DESCRIPTION: SEQ ID NO: 56:

```
ATG GGC CTC TCC ACC GTG CCT GAC CTG CTG CTG CCG CTG GTG CTC CTG      48
Met Gly Leu Ser Thr Val Pro Asp Leu Leu Leu Pro Leu Val Leu Leu
 1               5                  10                  15

GAG CTG TTG GTG GGA ATA TAC CCC TCA GGG GTT ATT GGA CTG GTC CCT      96
Glu Leu Leu Val Gly Ile Tyr Pro Ser Gly Val Ile Gly Leu Val Pro
            20                  25                  30

CAC CTA GGG GAC AGG GAG AAG AGA GAT AGT GTG TGT CCC CAA GGA AAA     144
His Leu Gly Asp Arg Glu Lys Arg Asp Ser Val Cys Pro Gln Gly Lys
        35                  40                  45

TAT ATC CAC CCT CAA AAT AAT TCG ATT TGC TGT ACC AAG TGC CAC AAA     192
Tyr Ile His Pro Gln Asn Asn Ser Ile Cys Cys Thr Lys Cys His Lys
    50                  55                  60

GGA ACC TAC TTG TAC AAT GAC TGT CCA GGC CCG GGG CAG GAT ACG GAC     240
Gly Thr Tyr Leu Tyr Asn Asp Cys Pro Gly Pro Gly Gln Asp Thr Asp
65                  70                  75                  80

TGC AGG GAG TGT GAG AGC GGC TCC TTC ACC GCT TCA GAA AAC CAC CTC     288
Cys Arg Glu Cys Glu Ser Gly Ser Phe Thr Ala Ser Glu Asn His Leu
                85                  90                  95

AGA CAC TGC CTC AGC TGC TCC AAA TGC CGA AAG GAA ATG GGT CAG GTG     336
Arg His Cys Leu Ser Cys Ser Lys Cys Arg Lys Glu Met Gly Gln Val
            100                 105                 110

GAG ATC TCT TCT TGC ACA GTG GAC CGG GAC ACC GTG TGT GGC TGC AGG     384
Glu Ile Ser Ser Cys Thr Val Asp Arg Asp Thr Val Cys Gly Cys Arg
        115                 120                 125

AAG AAC CAG TAC CGG CAT TAT TGG AGT GAA AAC CTT TTC CAG TGC TTC     432
Lys Asn Gln Tyr Arg His Tyr Trp Ser Glu Asn Leu Phe Gln Cys Phe
    130                 135                 140

AAT TGC AGC CTC TGC CTC AAT GGG ACC GTG CAC CTC TCC TGC CAG GAG     480
Asn Cys Ser Leu Cys Leu Asn Gly Thr Val His Leu Ser Cys Gln Glu
145                 150                 155                 160

AAA CAG AAC ACC GTG TGC ACC TGA                                     504
Lys Gln Asn Thr Val Cys Thr
                165
```

( 2 ) INFORMATION FOR SEQ ID NO: 57:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 57:

```
Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
            20                  25                  30
```

| | | | | | | | | | | | | | | |
|---|---|---|---|---|---|---|---|---|---|---|---|---|---|---|
| His | Leu | Gly<br>35 | Asp | Arg | Glu | Lys | Arg<br>40 | Asp | Ser | Val | Cys | Pro<br>45 | Gln | Gly | Lys |
| Tyr | Ile<br>50 | His | Pro | Gln | Asn | Asn<br>55 | Ser | Ile | Cys | Cys | Thr<br>60 | Lys | Cys | His | Lys |
| Gly<br>65 | Thr | Tyr | Leu | Tyr | Asn<br>70 | Asp | Cys | Pro | Gly | Pro<br>75 | Gly | Gln | Asp | Thr | Asp<br>80 |
| Cys | Arg | Glu | Cys | Glu<br>85 | Ser | Gly | Ser | Phe | Thr<br>90 | Ala | Ser | Glu | Asn | His<br>95 | Leu |
| Arg | His | Cys | Leu<br>100 | Ser | Cys | Ser | Lys | Cys<br>105 | Arg | Lys | Glu | Met | Gly<br>110 | Gln | Val |
| Glu | Ile | Ser<br>115 | Ser | Cys | Thr | Val | Asp<br>120 | Arg | Asp | Thr | Val | Cys<br>125 | Gly | Cys | Arg |
| Lys | Asn<br>130 | Gln | Tyr | Arg | His | Tyr<br>135 | Trp | Ser | Glu | Asn | Leu<br>140 | Phe | Gln | Cys | Phe |
| Asn<br>145 | Cys | Ser | Leu | Cys | Leu<br>150 | Asn | Gly | Thr | Val | His<br>155 | Leu | Ser | Cys | Gln | Glu<br>160 |
| Lys | Gln | Asn | Thr | Val<br>165 | Cys | Thr | | | | | | | | | |

We claim:

1. A DNA molecule which encodes a polypeptide which is capable of binding human TNFα and which has the first three cysteine-rich subdomains, but not the fourth cysteine-rich subdomain, of the extracellular binding domain of a receptor selected from the group consisting of the 55 kD and 75 kD receptors for human TNFα.

2. A DNA molecule according to claim 1, which has the nucleotide sequence of SEQ ID NO:3.

3. A DNA molecule according to claim 1, which has fused to the 5'-end thereof a sequence which encodes a signal amino acid sequence.

4. A DNA molecule according to claim 1, which has the nucleotide sequence of SEQ ID NO:1.

5. A DNA molecule according to claim 1, which is a vector and which is capable, when provided in a suitable host, of expressing said polypeptide.

6. A DNA molecule according to claim 5, which is a plasmid.

7. A host cell transformed with a DNA molecule as claimed in claim 5.

8. A host cell according to claim 7, which is a mammalian cell.

* * * * *